(12) United States Patent
Johnson et al.

(10) Patent No.: US 7,087,394 B2
(45) Date of Patent: Aug. 8, 2006

(54) METHODS AND COMPOSITIONS FOR TREATING AND DIAGNOSING DIABETES AND RELATED DISEASES INVOLVING BETA-TRP

(75) Inventors: Jeffrey D. Johnson, Moraga, CA (US); Yun-Ping Zhou, San Ramon, CA (US)

(73) Assignee: Metabolex, Inc., Hayward, CA (US)

( * ) Notice: Subject to any disclaimer, the term of this patent is extended or adjusted under 35 U.S.C. 154(b) by 0 days.

(21) Appl. No.: 10/794,897

(22) Filed: Mar. 4, 2004

(65) Prior Publication Data

US 2004/0259160 A1 Dec. 23, 2004

Related U.S. Application Data

(60) Provisional application No. 60/452,596, filed on Mar. 5, 2003.

(51) Int. Cl.
*G01N 33/53* (2006.01)
*C12N 15/63* (2006.01)
*A01N 38/00* (2006.01)

(52) U.S. Cl. .............................. 435/7.2; 435/455; 514/2
(58) Field of Classification Search .................... None
See application file for complete search history.

(56) References Cited

U.S. PATENT DOCUMENTS

| 5,932,417 | A | 8/1999 | Birnbaumer et al. |
| 2002/0081658 | A1 | 6/2002 | Curtis |
| 2002/0164645 | A1 | 11/2002 | Zuker et al. |
| 2005/0019830 | A1 | 1/2005 | Penner et al. |

FOREIGN PATENT DOCUMENTS

| WO | WO 01/32693 A2 | 5/2001 |
| WO | WO 02/059307 A1 | 8/2002 |

OTHER PUBLICATIONS

Thorens, Proc. Natl. Acad. Sci. USA 84: 8641-8645, 1992.*
Chan, Catherine B. et al.; "Overexpression of Uncoupling Protein 2 Inhibits Glucose-Stimulated Insulin Secretion From Rat Islets"; 1999, *Diabetes*, vol. 48, pp. 1482-1486.
Prawitt, Dirk et al.; "TRPM5 is a transient $Ca^{2+}$-activated cation channel responding to rapid changes in $[Ca^{2+}]I$"; 2003, *PNAS*, vol. 100, pp. 15166-15171.
Qian, Feng et al.; "Candidates for Nonselective Cation Channels and Store-Operated Channels in Insulin-Secreting Cells"; 2002, *Diabetes*, vol. 51, pp. S183-S189.
Roe, Michael W. et al.; "Characterization of a $Ca^{2+}$ Release-activated Nonselective Cation Current Regulating Membrane Potential and $[Ca^{2+}]I$ Oscillations"; 1998, *The Journal of Biological Chemistry*, vol. 273, No. 17, pp. 10402-10410.
Database WPI, Section Ch, week 200264, XP-002290296.
Clapham, David E. et al.; "The TRP Ion Channel Family"; 2002, *IUPHAR Compendium, TRP Channels*, pp. 1-37.
Perez, Christian A. et al.; "A transient receptor potential channel expressed in taste receptor cells"; 2002, *Nature Neuroscience*, vol. 5, No. 11, pp. 1169-1176.
Prawitt, Dirk et al.; "Identification and characterization of *MTR1*, a novel gene with homology to melastatin (MLSN1) and the *trp* gene family located in the BWS-WT2 critical region on chromosome 11p15.5 and showing allele-specific expression"; 2000, *Human Molecular Genetics*, vol. 9, No. 2, pp. 203-216.
Zhang, Yifeng et al.; "Coding of Sweet, Bitter, and Umami Tastes: Different Receptor Cells Sharing Similar Signaling Pathways"; 2003, *Cell*, vol. 112, pp. 293-301.
Irminger, J. et al. "Identification of differently expressed genes in islets of diabetic GK rats, using subtractive hybridization"; 2002, *38th EASD Annual Meeting*, Abstract #444, 1 page.

* cited by examiner

*Primary Examiner*—Eileen B. O'Hara
*Assistant Examiner*—Gyan Chandra
(74) *Attorney, Agent, or Firm*—Townsend and Townsend and Crew LLP

(57) ABSTRACT

Expression of beta-TRP is enriched in islet cells. Introduction of expression cassettes encoding beta-TRP into diabetic islet cells improved glucose-stimulated insulin production. Therefore, the invention provides methods of identifying beta-TRP modulators for treating diabetic individuals and introducing beta-TRP into islet cells

9 Claims, 11 Drawing Sheets

A: TRPM5 is relatively islet specific

B: TRPM5 is reduced in ZDF islets

Effects of ATP

Effects of Calcimycin

Figure 7A

```
                                  10                  20                  30
rat_betaTRP          M P M A Q S S C P G S P P D T G D G W E P V L C K G E V N F
mouse_TRPM5          M Q T T Q S S C P G S P P D T E D G W E P I L C R G E I N F
MBX_betaTRP_human    M Q D V Q G P R P G S P G D A E D R R E L G L H R G E V N
                     M Q   . Q S S C P G S P P D T E D G W E P . L C R G E V N F 40                  50                  60
rat_betaTRP          G G S G K K R S K F V K V P S N V A P S M L F E L L L T E W
mouse_TRPM5          G G S G K K R G K F V K V P S S V A P S V L F E L L L T E W
MBX_betaTRP_human    G G S G K K R G K N V R V P S G V A P S V L N D L L L A E W
                     G G S G K K R G K F V K V P S   V A P S V L F E L L L T E W 70                  80                  90
rat_betaTRP          H L P A P N L V V S L V G E E R L F A M K S W L R D V L R K
mouse_TRPM5          H L P A P N L V V S L V G E E R P L A M K S W L R D V L R K
MBX_betaTRP_human    H L P A P N L V V S L V G E E Q P F A M K S W L R D V L R K
                     H L P A P N L V V S L V G E E R P F A M K S W L R D V L R K 100                 110                 120
rat_betaTRP          G L V K A A Q S T G A W I L T S A L H V G L A R H V G Q A V
mouse_TRPM5          G L V K A A Q S T G A W I L T S A L H V G L A R H V G Q A V
MBX_betaTRP_human    G L V K A A Q S T G A W I L T S A L R V G L A R H V G Q A V
                     G L V K A A Q S T G A W I L T S A L H V G L A R H V G Q A V 130                 140                 150
rat_betaTRP          R D H S L A S T S T K V R V V A I G M A S L D R I L H R Q L
mouse_TRPM5          R D H S L A S T S T K I R V V A I G M A S L D R I L H R Q L
MBX_betaTRP_human    R D H S L A S T S T K V R V V A V G M A S L G R V L H R R I
                     R D H S L A S T S T K V R V V A I G M A S L D R I L H R Q L 160                 170                 180
rat_betaTRP          L D G V Q . . E D T P I H Y P A D E G S T Q G P L C P L D S
mouse_TRPM5          L D G V H Q K E D T P I H Y P A D E G N I Q G P L C P L D S
MBX_betaTRP_human    L E E A Q . . E D N P V H Y P E D D G S Q G P L C S L D S
                     L D G V Q     E D T P I H Y P A D E G   . Q G P L C P L D S 190                 200                 210
rat_betaTRP          N L S H F I L V E P G T L G S G N D G L A E L Q L S L E K H
mouse_TRPM5          N L S H F I L V E S G A L G S G N D G L T E L Q L S L E K H
MBX_betaTRP_human    N L S H F I L V E P G P P G K G - D G L T E L R L R L E K H
                     N L S H F I L V E P G   L G S G N D G L T E L Q L S L E K H 220                 230                 240
rat_betaTRP          I S Q Q R T G Y G G T S S I Q I P V L C L L V N G D P S T L
mouse_TRPM5          I S Q Q R T G Y G G T S C I Q I P V L C L L V N G D P N T L
MBX_betaTRP_human    I S E Q R A G Y G G T G S I E I P V L C L L V N G D P N T L
                     I S Q Q R T G Y G G T S S I Q I P V L C L L V N G D P N T L 250                 260                 270
rat_betaTRP          E R M S R A V E Q A A P W L I L A G S G G I A D V L A A L V
mouse_TRPM5          E R I S R A V E Q A A P W L I L A G S G G I A D V L A A L V
MBX_betaTRP_human    E R I S R A V E Q A A P W L I L V G S G G I A D V L A A L V
                     E R I S R A V E Q A A P W L I L A G S G G I A D V L A A L V 280                 290                 300
rat_betaTRP          G Q P H L L V P Q V T E K Q F R E K F P S E C F S W E A I V
mouse_TRPM5          S Q P H L L V P Q V A E K Q F R E K F P S E C F S W E A I V
MBX_betaTRP_human    N Q P H L L V P K V A E K Q N K E K F P S K H F S W E D I V
                       Q P H L L V P Q V A E K Q F R E K F P S E C F S W E A I V
```

Figure 7B

```
                          310                   320                   330
rat_betaTRP         H W T E L L Q N I A A H P H L L T V Y D F E Q E G S E D L D
mouse_TRPM5         H W T E L L Q N I A A H P H L L T V Y D F E Q E G S E D L D
MBX_betaTRP_human   R W T K L L Q N I T S H Q H L L T V Y D F E Q E G S E E L D
                    H W T E L L Q N I A A H P H L L T V Y D F E Q E G S E D L D 340                   350                   360
rat_betaTRP         T V I L K A L V K A C K S H S R D A Q D Y L D E L K L A V A
mouse_TRPM5         T V I L K A L V K A C K S H S Q E A Q D Y L D E L K L A V A
MBX_betaTRP_human   T V I L K A L V K A C K S H S Q E P Q D Y L D E L K L A V A
                    T V I L K A L V K A C K S H S Q E A Q D Y L D E L K L A V A 370                   380                   390
rat_betaTRP         W D R V D I A K S E I F N G D V E W K S C D L E E V M T D A
mouse_TRPM5         W D R V D I A K S E I F N G D V E W K S C D L E E V M T D A
MBX_betaTRP_human   W D R V D I A K S E I F N G D V E W K S C D L E E V M V D A
                    W D R V D I A K S E I F N G D V E W K S C D L E E V M T D A 400                   410                   420
rat_betaTRP         L V S N K P D F V R L F V D S G A D M A E F L T Y G R L Q Q
mouse_TRPM5         L V S N K P D F V R L F V D S G A D M A E F L T Y G R L Q Q
MBX_betaTRP_human   L V S N K P E N V R L N V D N G A D V A D F L T Y G R L Q E
                    L V S N K P D F V R L F V D S G A D M A E F L T Y G R L Q Q 430                   440                   450
rat_betaTRP         L Y H S V S P K S L L F E L L E R K H E E G R L T L A G L G
mouse_TRPM5         L Y H S V S P K S L L F E L L Q R K H E E G R L T L A G L G
MBX_betaTRP_human   L Y R S V S R K S L L F D L L Q R K Q E E A R L T L A G L G
                    L Y H S V S P K S L L F E L L Q R K H E E G R L T L A G L G 460                   470                   480
rat_betaTRP         A Q Q T R E L P V G L P A F S L H E V S R V L K D F L H D A
mouse_TRPM5         A Q Q A R E L P I G L P A F S L H E V S R V L K D F L H D A
MBX_betaTRP_human   T Q Q A R E P P A G P P A F S L H E V S R V L K D F L Q D A
                    A Q Q A R E L P . G L P A F S L H E V S R V L K D F L H D A 490                   500                   510
rat_betaTRP         C R G F Y Q D G R - - - - R M E E R G P P K R P A G Q K W L
mouse_TRPM5         C R G F Y Q D G R - - - - R M E E R G P P K R P A G Q K W L
MBX_betaTRP_human   C R G F Y Q D G R P G D R R R A E K G P A K R P T G Q K W L
                    C R G F Y Q D G R         R M E E R G P P K R P A G Q K W L 520                   530                   540
rat_betaTRP         P D L S R K S E D P W R D L F L W A V L Q N R Y E M A T Y F
mouse_TRPM5         P D L S R K S E D P W R D L F L W A V L Q N R Y E M A T Y F
MBX_betaTRP_human   L D L N Q K S E N P W R D L F L W A V L Q N R H E M A T Y F
                    P D L S R K S E D P W R D L F L W A V L Q N R Y E M A T Y F 550                   560                   570
rat_betaTRP         W A M G R E G V A A A L A A C K I I K E M S H L E K E A E V
mouse_TRPM5         W A M G R E G V A A A L A A C K I I K E M S H L E K E A E V
MBX_betaTRP_human   W A M G Q E G V A A A L A A C K I L K E M S H L E T E A E A
                    W A M G R E G V A A A L A A C K I I K E M S H L E K E A E V 580                   590                   600
rat_betaTRP         A R T M R E A K Y E Q L A L D L F S E C Y S N S E D R A F A
mouse_TRPM5         A R T M R E A K Y E Q L A L D L F S E C Y G N S E D R A F A
MBX_betaTRP_human   A R A T R E A K Y E R L A L D L F S E C Y S N S E A R A F A
                    A R T M R E A K Y E Q L A L D L F S E C Y S N S E D R A F A
```

Figure 7C

```
                            610                 620                 630
rat_betaTRP         L L V R R N H S W S R T T C L H L A T E A D A K A F F A H D
mouse_TRPM5         L L V R R N H S W S R T T C L H L A T E A D A K A F F A H D
MBX_betaTRP_human   L L V R R N R C W S K T T C L H L A T E A D A K A F N A H D
                    L L V R R N H S W S R T T C L H L A T E A D A K A F F A H D 640                 650                 660
rat_betaTRP         G V Q A F L T K I W W G D M A T G T P I L R L L G A F T C P
mouse_TRPM5         G V Q A F L T K I W W G D M A T G T P I L R L L G A F T C P
MBX_betaTRP_human   G V Q A F L T R I W W G D M A A G T P I L R L L G A F L C P
                    G V Q A F L T K I W W G D M A T G T P I L R L L G A F T C P 670                 680                 690
rat_betaTRP         A L I Y T N L I S F S E D A P Q R M D L E D L Q E P D S L D
mouse_TRPM5         A L I Y T N L I S F S E D A P Q R M D L E D L Q E P D S L D
MBX_betaTRP_human   A L V Y T N L I T F S E E A P L R T G L E D L Q D L D S L D
                    A L I Y T N L I S F S E D A P Q R M D L E D L Q E P D S L D 700                 710                 720
rat_betaTRP         M E K S F L C S H G G Q L E K L T E A P R A P - G D L G P Q A
mouse_TRPM5         M E K S F L C S R G G Q L E K L T E A P R A P G D L G P Q A
MBX_betaTRP_human   T E K S P L Y G L Q S R V E E L V E A P R A Q G D R G P R A
                    M E K S F L C S . G G Q L E K L T E A P R A P G D L G P Q A 730                 740                 750
rat_betaTRP         A F L L T W R K F W G A P V T V F L G N V V M Y F A F L F
mouse_TRPM5         A F L L T W R K F W G A P V T V F L G N V V M Y F A F L F
MBX_betaTRP_human   V F L L T W R K F W G A P V T V F L G N V V M Y F A F L F
                    A F L L T W R K F W G A P V T V F L G N V V M Y F A F L F 760                 770                 780
rat_betaTRP         L F S Y V L L V D F R P P P Q G P S G S E V T L Y F W V F T
mouse_TRPM5         L F T Y V L L V D F R P P P Q G P S G S E V T L Y F W V F T
MBX_betaTRP_human   L F T Y V L L V D F R P P P Q G P S G P E V T L Y F W V N T
                    L F T Y V L L V D F R P P P Q G P S G S E V T L Y F W V F T 790                 800                 810
rat_betaTRP         L V L E E I R Q G F F T N E D T R L V K K F T L Y V E D N W
mouse_TRPM5         L V L E E I R Q G F F T D E D T R L V K K F T L Y V E D N W
MBX_betaTRP_human   L V L E E I R Q G F F T D E D T H L V K K F T L Y V G D N W
                    L V L E E I R Q G F F T D E D T H L V K K F T L Y V E D N W 820                 830                 840
rat_betaTRP         N K C D M V A I F L F I V G V T C R M V P S V F E A G R T V
mouse_TRPM5         N K C D M V A I F L F I V G V T C R M V P S V F E A G R T V
MBX_betaTRP_human   N K C D M V A I F L F I V G V T C R M L P S A N E A G R T V
                    N K C D M V A I F L F I V G V T C R M V P S V F E A G R T V 850                 860                 870
rat_betaTRP         L A I D F M V F T L R L I H I F A I H K Q L G P K I I I V E
mouse_TRPM5         L A I D F M V F T L R L I H I F A I H K Q L G P K I I I V E
MBX_betaTRP_human   L A M D F M V F T L R L I H I N A I H K Q L G P K I I V V E
                    L A I D F M V F T L R L I H I F A I H K Q L G P K I I I V E 880                 890                 900
rat_betaTRP         R M M K D V F F F L F F L S V W L V A Y G V T T Q A L L H P
mouse_TRPM5         R M M K D V F F F L F F L S V W L V A Y G V T T Q A L L H P
MBX_betaTRP_human   R M M K D V F F F L F N L S V W L V A Y G V T T Q A L L H P
                    R M M K D V F F F L F F L S V W L V A Y G V T T Q A L L H P
```

Figure 7D

|  | 910 | 920 | 930 |
|---|---|---|---|
| rat_betaTRP | H D G R L E W I F R R V L Y R P Y L Q I F G Q I P L D E I D |
| mouse_TRPM5 | H D G R L E W I F R R V L Y R P Y L Q I F G Q I P L D E I D |
| MBX_betaTRP_human | H D G R L E W I F R R V L Y R P Y L Q I F G Q I P L D E I D |
|  | H D G R L E W I F R R V L Y R P Y L Q I F G Q I P L D E I D |

|  | 940 | 950 | 960 |
|---|---|---|---|
| rat_betaTRP | E A R V N C S L H P L L L D S S A S C P N L Y A N W L V I L |
| mouse_TRPM5 | E A R V N C S L H P L L L E S S A S C P N L Y A N W L V I L |
| MBX_betaTRP_human | E A R V N C S T H P L L L E D S P S C P S L Y A N W L V I L |
|  | E A R V N C S L H P L L L E S S A S C P N L Y A N W L V I L |

|  | 970 | 980 | 990 |
|---|---|---|---|
| rat_betaTRP | L L V T F L L V T N V L L M N L L I A M F S Y T F Q V V Q G |
| mouse_TRPM5 | L L V T F L L V T N V L L M N L L I A M F S Y T F Q V V Q G |
| MBX_betaTRP_human | L L V T F L L V T N V L L M N L L I A M F S Y T F Q V V Q G |
|  | L L V T F L L V T N V L L M N L L I A M F S Y T F Q V V Q G |

|  | 1000 | 1010 | 1020 |
|---|---|---|---|
| rat_betaTRP | N A D M F W K F Q R Y H L I V E Y H G R P A L A P P F I L L |
| mouse_TRPM5 | N A D M F W K F Q R Y H L I V E Y H G R P A L A P P F I L L |
| MBX_betaTRP_human | N A D M F W K F Q R Y N L I V E Y H E R P A L A P P F I L L |
|  | N A D M F W K F Q R Y H L I V E Y H G R P A L A P P F I L L |

|  | 1030 | 1040 | 1050 |
|---|---|---|---|
| rat_betaTRP | S H L S L V L K Q V F R K E A Q H K Q Q H L E R D L P D P V |
| mouse_TRPM5 | S H L S L V L K Q V F R K E A Q H K R Q H L E R D L P D P L |
| MBX_betaTRP_human | S H L S L T L R R V F K K E A E H K R E H L E R D L P D P L |
|  | S H L S L V L K Q V F R K E A Q H K R Q H L E R D L P D P L |

|  | 1060 | 1070 | 1080 |
|---|---|---|---|
| rat_betaTRP | D Q K I I T W E T V Q K E N F L S T M E K R R D S E E V |
| mouse_TRPM5 | D Q K I I T W E T V Q K E N F L S T M E K R R D S E G E V |
| MBX_betaTRP_human | D Q K V V T W E T V Q K E N F L S K M E K R R D S E G E V |
|  | D Q K I I T W E T V Q K E N F L S T M E K R R D S E G E V |

|  | 1090 | 1100 | 1110 |
|---|---|---|---|
| rat_betaTRP | L R K T A H R V D L I A K Y I G G L R E Q E K R I K C L E S |
| mouse_TRPM5 | L R K T A H R V D L I A K Y I G G L R E Q E K R I K C L E S |
| MBX_betaTRP_human | L R K T A H R V D F I A K Y L G G L R E Q E K R I K C L E S |
|  | L R K T A H R V D L I A K Y I G G L R E Q E K R I K C L E S |

|  | 1120 | 1130 | 1140 |
|---|---|---|---|
| rat_betaTRP | Q A N Y C M L L L S S M T D T L A P G G T Y S S S Q N C G R |
| mouse_TRPM5 | Q A N Y C M L L L S S M T D T L A P G G T Y S S S Q N C G C |
| MBX_betaTRP_human | Q I N Y C S V L V S S V A D V L A Q G G G P R S S Q H C G E |
|  | Q A N Y C M L L L S S M T D T L A P G G T Y S S S Q N C G |

|  | 1150 | 1160 | 1170 |
|---|---|---|---|
| rat_betaTRP | R S Q P A S A R D R - - - - - - E Y L E A G L P H S D T |
| mouse_TRPM5 | R S Q P A S A R D R - - - - - - E Y L E S G L P P S D T |
| MBX_betaTRP_human | G S Q L V A D H R G G L D G W E Q P G A G Q P P S D T |
|  | R S Q P A S A R D R       E Y L E A G L P P S D T |

Figure 8

MQDVQGPRPGSPGDAEDRRELGLHRGEVNFGGSGKKRGKFVRVPSGVAPSVLFDLL
LAEWHLPAPNLVVSLVGEEQPFAMKSWLRDVLRKGLVKAAQSTGAWILTSALRVG
LARHVGQAVRDHSLASTSTKVRVVAVGMASLGRVLHRRILEEAQVHEDFPVHYPED
DGGSQGPLCSLDSNLSHFILVEPGPPGKGDGLTELRLRLEKHISEQRAGYGGTGSIEIP
VLCLLVNGDPNTLERISRAVEQAAPWLILVGSGGIADVLAALVNQPHLLVPKVAEKQ
FKEKFPSKHFSWEDIVRWTKLLQNITSHQHLLTVYDFEQEGSEELDTVILKALVKAC
KSHSQEPQDYLDELKLAVAWDRVDIAKSEIFNGDVEWKSCDLEEVMVDALVSNKPE
FVRLFVDNGADVADFLTYGRLQELYRSVSRKSLLFDLLQRKQEEARLTLAGLGTQQ
AREPPAGPPAFSLHEVSRVLKDFLQDACRGFYQDGRPGDRRRAEKGPAKRPTGQKW
LLDLNQKSENPWRDLFLWAVLQNRHEMATYFWAMGQEGVAAALAACKILKEMSH
LETEAEAARATREAKYEQLALDLFSECYSNSEARAFALLVRRNRCWSKTTCLHLATE
ADAKAFFAHDGVQAFLTRIWWGDMAAGTPILRLLGAFLCPALVYTNLITFSEEAPLR
TGLEDLQDLDSLDTEKSPLYGLQSRVEELVEAPRAQGDRGPRAVFLLTRWRKFWGA
PVTVFLGNVVMYFAFLFLFTYVLLVDFRPPPQGPSGPEVTLYFWVFTLVLEEIRQGFF
TDEDTHLVKKFTLYVGDNWNKCDMVAIFLFIVGVTCRMLPSAFEAGRTVLAMDFM
VFTLRLIHIFAIHKQLGPKIIVVERMMKDVFFFLFFLSVWLVAYGVTTQALLHPHDGR
LEWIFRRVLYRPYLQIFGQIPLDEIDEARVNCSTHPLLLEDSPSCPSLYANWLVILLLV
TFLLVTNVLLMNLLIAMFSYTFQVVQGNADMFWKFQRYNLIVEYHERPALAPPFILL
SHLSLTLRRVFKKEAEHKREHLERDLPDPLDQKVVTWETVQKENFLSKMEKRRRDS
EGEVLRKTAHRVDFIAKYLGGLREQEKRIKCLESQINYCSVLVSSVADVLAQGGGPR
SSQHCGEGSQLVAADHRGGLDGWEQPGAGQPPSDT

SEQUENCE LISTING

```
<160> NUMBER OF SEQ ID NOS: 9

<210> SEQ ID NO 1
<211> LENGTH: 3931
<212> TYPE: DNA
<213> ORGANISM: Homo sapiens
<220> FEATURE:
<223> OTHER INFORMATION: human betaTRP (MTR1) calcium channel

<400> SEQUENCE: 1
gaggccacca tgcaggatgt ccaaggcccc cgtcccggaa gccccgggga tgctgaagac      60
cggcgggagc tgggcttgca caggggcgag gtcaactttg gagggtctgg gaagaagcga     120
ggcaagtttg tacgggtgcc gagcggagtg gccccgtctg tgctctttga cctgctgctt     180
gctgagtggc acctgccggc ccccaacctg gtggtgtccc tggtgggtga ggagcagcct     240
ttcgccatga agtcctggct gcgggatgtg ctgcgcaagg ggctggtgaa ggcggctcag     300
```

```
agcacaggag cctggatcct gaccagtgcc ctccgcgtgg gcctggccag gcatgtcggg    360
caggccgtgc gcgaccactc gctggccagc acgtccacca aggtccgtgt ggttgctgtc    420
ggcatggcct cgctgggccg cgtcctgcac cgccgcattc tggaggaggc ccaggtgcac    480
gaggattttc ctgtccacta ccctgaggat gacggcggca gccagggccc cctctgttca    540
ctggacagca acctctccca cttcatcctg gtggagccag gcccccggga agggcgat     600 gggctgacgg agctgcggct gaggctggag aagcacatct cggagcagag gcgggctac    660 gggggcactg gcagcatcga gatccctgtc ctctgcttgc tggtcaatgg tgatcccaac    720
accttggaga ggatctccag ggccgtggag caggctgccc cgtggctgat cctggtaggc    780 tcgggggggca tcgccgatgt gcttgctgcc ctagtgaacc agccccacct cctggtgccc    840
aaggtggccg agaagcagtt taaggagaag ttccccagca agcatttctc ttgggaggac    900
atcgtgcgct ggaccaagct gctgcagaac atcacctcac accagcacct gctcaccgtg    960
tatgacttcg agcaggaggg ctccgaggag ctggacacgg tcatcctgaa ggcgctggtg    1020
aaagcctgca agagccacag ccaggagcct caggactatc tggatgagct caagctggcc    1080
gtggcctggg accgcgtgga catcgccaag agtgagatct caatggggga cgtggagtgg    1140
aagtcctgtg acctggagga ggtgatggtg gacgccctgg tcagcaacaa gcccgagttt    1200
gtgcgcctct ttgtggacaa cggcgcagac gtggccgact tcctgacgta tgggcggctg    1260
caggagctct accgctccgt gtcacgcaag agcctgctct tcgacctgct gcagcggaag    1320
caggaggagg cccggctgac gctggccggc ctgggcaccc agcaggcccg ggagccaccc    1380
gcggggccac cggccttctc cctgcacgag gtctcccgcg tactcaagga cttcctgcag    1440
gacgcctgcc gaggcttcta ccaggacggc cggccagggg accgcaggag ggcggagaag    1500
ggcccggcca gcggcccac gggccagaag tggctgctgg acctgaacca aagagcgag    1560 aaccctggc gggaccctgtt cctgtgggcc gtgctgcaga accgcacga gatggccacc    1620 tacttctggg ccatgggcca ggaaggtgtg gcagccgcac tggccgcctg caaaatcctc    1680
aaagagatgt cgcacctgga gacggaggcc gaggcggccc gagccacgcg cgaggcgaaa    1740
tacgagcagc tggccctcga cctcttctcc gagtgctaca gcaacagtga ggcccgcgcc    1800
ttcgccctgc tggtgcgccg gaaccgctgc tggagcaaga ccacctgcct gcacctggcc    1860
accgaggctg acgccaaggc cttctttgcc cacgacggcg ttcaggcctt cctgaccagg    1920
atctggtggg gggacatggc cgcaggcacg cccatcctgc ggctgctagg agccttcctc    1980
tgccccgccc tcgtctatac caacctcatc accttcagtg aggaagctcc cctgaggaca    2040
ggcctggagg acctgcagga cctggacagc ctggacacgg agaagagccc gctgtatggc    2100
ctgcagagcc gggtggagga gctggtggag gcgccgaggc tcagggtga ccgaggccca    2160 cgtgctgtct tcctgctcac acgctggcgg aaattctggg gcgctcccgt gactgtgttc    2220
ctggggaacg tggtcatgta cttcgccttc ctcttcctgt tcacctacgt cctgctggtg    2280
gacttcaggc cgccccccca gggcccctca gggcccgagg tcaccctcta cttctgggtc    2340
tttacgctgg tgctggagga aatccggcag ggcttcttca cagacgagga cacacacctg    2400
gtgaagaagt tcacactgta tgtgggggac aactggaaca agtgtgacat ggtggccatc    2460
ttcctgttca tcgtgggtgt cacctgcagg atgctgccgt cggcgtttga ggctggccgc    2520
acagtcctcg ccatggactt catggtgttc acgctgcggc tgatccatat ctttgccata    2580
cacaagcagc tggccccaa gatcatcgtg gtagagcgca tgatgaagga cgtcttcttc    2640
ttcctcttct ttctgagcgt gtggctcgtg gcctacggtg tcaccaccca ggcgctgctg    2700
```

-continued

```
caccccatg acggccgcct ggagtggatc ttccgccggg tgctctaccg gccctacctg      2760
cagatcttcg ccagatccc actggacgag attgatgaag cccgtgtgaa ctgctccacc      2820
cacccactgc tgctggagga ctcaccatcc tgcccagcc tctatgccaa ctggctggtc      2880
atcctcctgc tggtcacctt cctgttggtc accaatgtgc tgctcatgaa cctgctcatc      2940
gccatgttca gctacacgtt ccaggtggtg cagggcaacg cagacatgtt ctggaagttc      3000
cagcgctaca acctgattgt ggagtaccac gagcgccccg ccctggcccc gcccttcatc      3060
ctgctcagcc acctgagcct gacgctccgc cgggtcttca agaaggaggc tgagcacaag      3120
cgggagcacc tggagagaga cctgccagac cccctggacc agaaggtcgt cacctgggag      3180
acagtccaga aggagaactt cctgagcaag atggagaagc ggaggaggga cagcgagggg      3240
gaggtgctgc ggaaaaccgc ccacagagtg gacttcattg ccaagtacct cggggtctg      3300 agagagcaag aaaagcgcat caagtgtctg gagtcacaga tcaactactg ctcggtgctc      3360
gtgtcctccg tggctgacgt gctggcccag ggtggcggcc cccggagctc tcagcactgt      3420
ggcgagggaa gccagctggt ggctgctgac cacagaggtg gtttagatgg ctgggaacaa      3480 cccgggctg gccagcctcc ctcggacacc tgagctgctt ggcctgccac gtgtggggcc      3540
acctctcctc agctgccac cctgcacgtt gtgcactgac ctttgccgac ctccagcgga      3600
accccccagg gggcaccagc ccccagcag acaatggccc tcctggtgcc tcaccacaga      3660
ccctcaccca aggaaccgc tccttgtccc tcctggcctc cccggaggca cagcagtgtc      3720
atggggctgt ctccctgac aggcacaact ccccgggcag aaaacgtgcc ccaccggcat      3780
ccctacctgg aaactgacca gcctgcactg tggaaaagct ggccctgtgg cgtgacgggg      3840
gagcaccccc atccagactg cgaagctgct ctggggtctg cacccacccc tgccctgact      3900
tgtgttgcct gacaagagac tcatcttttt t                                    3931
```

<210> SEQ ID NO 2
<211> LENGTH: 1167
<212> TYPE: PRT
<213> ORGANISM: Homo sapiens
<220> FEATURE:
<223> OTHER INFORMATION: human betaTRP (MTR1) calcium channel

<400> SEQUENCE: 2

```
Met Gln Asp Val Gln Gly Pro Arg Pro Gly Ser Pro Gly Asp Ala Glu
 1               5                  10                  15

Asp Arg Arg Glu Leu Gly Leu His Arg Gly Glu Val Asn Phe Gly Gly
            20                  25                  30

Ser Gly Lys Lys Arg Gly Lys Phe Val Arg Val Pro Ser Gly Val Ala
        35                  40                  45

Pro Ser Val Leu Phe Asp Leu Leu Ala Glu Trp His Leu Pro Ala
    50                  55                  60

Pro Asn Leu Val Val Ser Leu Val Gly Glu Glu Gln Pro Phe Ala Met
65                  70                  75                  80

Lys Ser Trp Leu Arg Asp Val Leu Arg Lys Gly Leu Val Lys Ala Ala
                85                  90                  95

Gln Ser Thr Gly Ala Trp Ile Leu Thr Ser Ala Leu Arg Val Gly Leu
            100                 105                 110

Ala Arg His Val Gly Gln Ala Val Arg Asp His Ser Leu Ala Ser Thr
        115                 120                 125

Ser Thr Lys Val Arg Val Val Ala Val Gly Met Ala Ser Leu Gly Arg
    130                 135                 140
```

-continued

```
Val Leu His Arg Arg Ile Leu Glu Glu Ala Gln Val His Glu Asp Phe
145                 150                 155                 160

Pro Val His Tyr Pro Glu Asp Gly Gly Ser Gln Gly Pro Leu Cys
            165                 170                 175

Ser Leu Asp Ser Asn Leu Ser His Phe Ile Leu Val Glu Pro Gly Pro
            180                 185                 190

Pro Gly Lys Gly Asp Gly Leu Thr Glu Leu Arg Leu Arg Leu Glu Lys
            195                 200                 205

His Ile Ser Glu Gln Arg Ala Gly Tyr Gly Gly Thr Gly Ser Ile Glu
    210                 215                 220

Ile Pro Val Leu Cys Leu Leu Val Asn Gly Asp Pro Asn Thr Leu Glu
225                 230                 235                 240

Arg Ile Ser Arg Ala Val Glu Gln Ala Ala Pro Trp Leu Ile Leu Val
                245                 250                 255

Gly Ser Gly Gly Ile Ala Asp Val Leu Ala Ala Leu Val Asn Gln Pro
                260                 265                 270

His Leu Leu Val Pro Lys Val Ala Glu Lys Gln Phe Lys Glu Lys Phe
    275                 280                 285

Pro Ser Lys His Phe Ser Trp Glu Asp Ile Val Arg Trp Thr Lys Leu
290                 295                 300

Leu Gln Asn Ile Thr Ser His Gln His Leu Leu Thr Val Tyr Asp Phe
305                 310                 315                 320

Glu Gln Glu Gly Ser Glu Glu Leu Asp Thr Val Ile Leu Lys Ala Leu
                325                 330                 335

Val Lys Ala Cys Lys Ser His Ser Gln Glu Pro Gln Asp Tyr Leu Asp
                340                 345                 350

Glu Leu Lys Leu Ala Val Ala Trp Asp Arg Val Asp Ile Ala Lys Ser
                355                 360                 365

Glu Ile Phe Asn Gly Asp Val Glu Trp Lys Ser Cys Asp Leu Glu Glu
                370                 375                 380

Val Met Val Asp Ala Leu Val Ser Asn Lys Pro Glu Phe Val Arg Leu
385                 390                 395                 400

Phe Val Asp Asn Gly Ala Asp Val Ala Asp Phe Leu Thr Tyr Gly Arg
                405                 410                 415

Leu Gln Glu Leu Tyr Arg Ser Val Ser Arg Lys Ser Leu Leu Phe Asp
                420                 425                 430

Leu Leu Gln Arg Lys Gln Glu Glu Ala Arg Leu Thr Leu Ala Gly Leu
            435                 440                 445

Gly Thr Gln Gln Ala Arg Glu Pro Pro Ala Gly Pro Pro Ala Phe Ser
    450                 455                 460

Leu His Glu Val Ser Arg Val Leu Lys Asp Phe Leu Gln Asp Ala Cys
465                 470                 475                 480

Arg Gly Phe Tyr Gln Asp Gly Arg Pro Gly Asp Arg Arg Ala Glu
                485                 490                 495

Lys Gly Pro Ala Lys Arg Pro Thr Gly Gln Lys Trp Leu Leu Asp Leu
            500                 505                 510

Asn Gln Lys Ser Glu Asn Pro Trp Arg Asp Leu Phe Leu Trp Ala Val
            515                 520                 525

Leu Gln Asn Arg His Glu Met Ala Thr Tyr Phe Trp Ala Met Gly Gln
            530                 535                 540

Glu Gly Val Ala Ala Ala Leu Ala Ala Cys Lys Ile Leu Lys Glu Met
545                 550                 555                 560
```

-continued

```
Ser His Leu Glu Thr Glu Ala Glu Ala Arg Ala Thr Arg Glu Ala
            565                 570                 575

Lys Tyr Glu Gln Leu Ala Leu Asp Leu Phe Ser Glu Cys Tyr Ser Asn
            580                 585                 590

Ser Glu Ala Arg Ala Phe Ala Leu Leu Val Arg Arg Asn Arg Cys Trp
            595                 600                 605

Ser Lys Thr Thr Cys Leu His Leu Ala Thr Glu Ala Asp Ala Lys Ala
            610                 615                 620

Phe Phe Ala His Asp Gly Val Gln Ala Phe Leu Thr Arg Ile Trp Trp
625                 630                 635                 640

Gly Asp Met Ala Ala Gly Thr Pro Ile Leu Arg Leu Leu Gly Ala Phe
                645                 650                 655

Leu Cys Pro Ala Leu Val Tyr Thr Asn Leu Ile Thr Phe Ser Glu Glu
                660                 665                 670

Ala Pro Leu Arg Thr Gly Leu Glu Asp Leu Gln Asp Leu Asp Ser Leu
                675                 680                 685

Asp Thr Glu Lys Ser Pro Leu Tyr Gly Leu Gln Ser Arg Val Glu Glu
            690                 695                 700

Leu Val Glu Ala Pro Arg Ala Gln Gly Asp Arg Gly Pro Arg Ala Val
705                 710                 715                 720

Phe Leu Leu Thr Arg Trp Arg Lys Phe Trp Gly Ala Pro Val Thr Val
                725                 730                 735

Phe Leu Gly Asn Val Val Met Tyr Phe Ala Phe Leu Phe Leu Phe Thr
                740                 745                 750

Tyr Val Leu Leu Val Asp Phe Arg Pro Pro Gln Gly Pro Ser Gly
                755                 760                 765

Pro Glu Val Thr Leu Tyr Phe Trp Val Phe Thr Leu Val Leu Glu Glu
            770                 775                 780

Ile Arg Gln Gly Phe Phe Thr Asp Glu Asp Thr His Leu Val Lys Lys
785                 790                 795                 800

Phe Thr Leu Tyr Val Gly Asp Asn Trp Asn Lys Cys Asp Met Val Ala
                805                 810                 815

Ile Phe Leu Phe Ile Val Gly Val Thr Cys Arg Met Leu Pro Ser Ala
                820                 825                 830

Phe Glu Ala Gly Arg Thr Val Leu Ala Met Asp Phe Met Val Phe Thr
            835                 840                 845

Leu Arg Leu Ile His Ile Phe Ala Ile His Lys Gln Leu Gly Pro Lys
            850                 855                 860

Ile Ile Val Val Glu Arg Met Met Lys Asp Val Phe Phe Phe Leu Phe
865                 870                 875                 880

Phe Leu Ser Val Trp Leu Val Ala Tyr Gly Val Thr Thr Gln Ala Leu
                885                 890                 895

Leu His Pro His Asp Gly Arg Leu Glu Trp Ile Phe Arg Arg Val Leu
                900                 905                 910

Tyr Arg Pro Tyr Leu Gln Ile Phe Gly Gln Ile Pro Leu Asp Glu Ile
            915                 920                 925

Asp Glu Ala Arg Val Asn Cys Ser Thr His Pro Leu Leu Leu Glu Asp
            930                 935                 940

Ser Pro Ser Cys Pro Ser Leu Tyr Ala Asn Trp Leu Val Ile Leu Leu
945                 950                 955                 960

Leu Val Thr Phe Leu Leu Val Thr Asn Val Leu Leu Met Asn Leu Leu
                965                 970                 975

Ile Ala Met Phe Ser Tyr Thr Phe Gln Val Val Gln Gly Asn Ala Asp
```

-continued

```
               980                 985                 990
Met Phe Trp Lys Phe Gln Arg Tyr Asn Leu Ile Val Glu Tyr His Glu
           995                1000               1005
Arg Pro Ala Leu Ala Pro Pro Phe Ile Leu Leu Ser His Leu Ser Leu
       1010                1015                1020
Thr Leu Arg Arg Val Phe Lys Lys Glu Ala Glu His Lys Arg Glu His
1025                1030                1035                1040
Leu Glu Arg Asp Leu Pro Asp Pro Leu Asp Gln Lys Val Val Thr Trp
               1045                1050                1055
Glu Thr Val Gln Lys Glu Asn Phe Leu Ser Lys Met Glu Lys Arg Arg
           1060                1065                1070
Arg Asp Ser Glu Gly Glu Val Leu Arg Lys Thr Ala His Arg Val Asp
       1075                1080                1085
Phe Ile Ala Lys Tyr Leu Gly Gly Leu Arg Glu Gln Glu Lys Arg Ile
       1090                1095                1100
Lys Cys Leu Glu Ser Gln Ile Asn Tyr Cys Ser Val Leu Val Ser Ser
1105                1110                1115                1120
Val Ala Asp Val Leu Ala Gln Gly Gly Gly Pro Arg Ser Ser Gln His
               1125                1130                1135
Cys Gly Glu Gly Ser Gln Leu Val Ala Ala Asp His Arg Gly Gly Leu
           1140                1145                1150
Asp Gly Trp Glu Gln Pro Gly Ala Gly Gln Pro Pro Ser Asp Thr
       1155                1160                1165

<210> SEQ ID NO 3
<211> LENGTH: 4608
<212> TYPE: DNA
<213> ORGANISM: Mus musculus
<220> FEATURE:
<223> OTHER INFORMATION: mouse betaTRP (TRPM5) calcium channel

<400> SEQUENCE: 3
atgcaaacaa cccagagctc ctgccccggc agccccccag atactgagga tggctgggag      60
cccatcctat gcaggggaga gatcaacttc ggagggtctg ggaagaagcg aggcaagttt     120
gtgaaggtgc caagcagtgt ggccccctcc gtgcttttg aactcctgct caccgagtgg      180
cacctgccag cccccaacct ggtggtgtcc ctggtgggtg aggaacgacc tttggctatg     240
aagtcgtggc ttcgggatgt cctgcgcaag gggctggtga agcagctca gagcacaggt      300 gcctggatcc tgaccagtgc cctccacgtg gcctggccc ccatgttgg acaagctgta       360 cgtgatcact ctctggctag cacatccacc aagatccgtg tagtggccat cggaatggcc    420
tctctggatc gaatccttca ccgtcaactt ctagatggtg tccaccaaaa ggaggatact    480
cccatccact acccagcaga tgagggcaac attcaggac ccctctgccc cctggacagc      540
aatctctccc acttcatcct tgtggagtca ggcgcccttg ggagtgggaa cgacgggctg    600
acagagctgc agctgagcct ggagaagcac atctctcagc agaggacagg ttatggggc     660 accagctgca tccagatacc tgtcctttgc ctgttggtca atggtgaccc caacaccta    720 gagaggattt ccagggcagt ggagcaggct gccccatggc tgatcctggc aggttctggt    780
ggcattgctg atgtactcgc tgccctggta agccagcctc atctcctggt gccccaggtg    840
gctgagaagc agttcagaga gaaattccc agcgagtgtt tctcttggga agccattgta    900
cactggacag agctgttaca gaacattgct gcacaccccc acctgctcac agtatatgac    960
ttcgagcagg agggttcgga ggacctggac actgtcatcc tcaaggcact tgtgaaagcc   1020
```

-continued

```
tgcaagagcc acagccaaga agcccaagac tacctagatg agctcaagtt agcagtggcc    1080
tgggatcgcg tggacattgc caagagtgaa atcttcaatg ggacgtgga atggaagtcc    1140
tgtgacttgg aagaggtgat gacagatgcc ctcgtgagca acaagcctga ctttgtccgc    1200
ctctttgtgg acagcggtgc tgacatggcc gagttcttga cctatgggcg gctgcagcag    1260
ctttaccatt ctgtgtcccc caagagcctc ctctttgaac tgctgcagcg taagcatgag    1320
gagggtaggc tgacactggc cggcctgggt gcccagcagg ctcgggagct gcccattggt    1380
ctgcctgcct tctcactcca cgaggtctcc cgcgtactca agacttcct gcatgacgcc     1440
tgccgtggct tctaccagga cgggcgcagg atggaggaga gagggccacc taagcggccc    1500
gcaggccaga agtggctgcc agacctcagt aggaagagtg aagacccttg agggacctg     1560
ttcctctggg ctgtgctgca gaatcgttat gagatggcca catacttctg gccatgggc     1620
cgggagggtg tggctgctgc tctggctgcc tgcaagatca taaggaaat gtcccacctg     1680
gagaaagagg cagaggtggc ccgcaccatg cgtgaggcca gtatgagca gctggccctg    1740
gatcttttct cagagtgcta cggcaacagt gaggaccgtg cctttgccct gctggtgcga    1800
aggaaccaca gctggagcag gaccacgtgc ctgcacctgg ccactgaagc tgatgccaag    1860
gccttctttg cccatgacgg tgtgcaagca ttcctgacca agatctggtg gggagacatg    1920
gccacaggca cacccatcct acggcttctg ggtgccttca cctgcccagc cctcatctac    1980
acaaacctca tctccttcag tgaggatgcc ccgcagagga tggacctaga agatctgcag    2040
gagccagaca gcttggatat ggaaaagagc ttcctatgca gccggggtgg ccaattggag    2100
aagctaacag aggcaccaag ggctccaggc gatctaggcc cacaagctgc cttcctgctc    2160
acacggtgga ggaagttctg gggcgctcct gtgactgtgt tcctggggaa tgtggtcatg    2220
tacttcgcat tcctcttcct gttcacctat gtcctgctgg tggacttcag gccaccaccc    2280
cagggcccgt ctggatccga ggttacccctc tatttctggg tgttcacact ggtgctggag    2340
gaaatccgac agggcttctt cacagatgag gacacgcacc tggtgaagaa attcactctg    2400
tatgtggaag acaactggaa caagtgtgac atggtggcca tcttcctgtt cattgtggga    2460
gtcacctgta gaatggtgcc ctcggtgttt gaggctggca ggaccgttct ggccattgac    2520
ttcatggtgt tcacacttcg gctcatccac atctttgcta ttcacaagca gttgggtcct    2580
aagatcatca ttgtagagcg aatgatgaag gatgtcttct ttttcctctt cttcctgagc    2640
gtatggcttg tggcctatgg tgtgaccact caggccctgc tgcatcccca tgatggccgt    2700
ttggagtgga ttttccgccg tgtgctatac aggccttacc tgcagatctt tgggcaaatc    2760
cctctggatg aaattgatga ggctcgtgtg aactgttctc ttcaccctct gctgctggaa    2820
agctcggctt cctgccctaa tctctatgcc aactggctgg tcattctcct gctggttacc    2880
ttcctgcttg tcactaatgt gctgctcatg aaccttctga tcgccatgtt cagctacaca    2940
ttccaggtgg tgcaaggcaa tgcagacatg ttctggaagt tcaacgcta ccacctcatc    3000
gttgaatacc atggaagacc agctctggcc ccgcccttca tcctgctcag ccacctgagc    3060
ctggtgctca gcaggtctt caggaaggaa gcccagcata gcgacaaca tctggagaga    3120
gacttgcctg acccccttgga ccagaagatc attacctggg aaacggttca aaggagaac    3180
ttcctgagta ccatggagaa acggaggagg gacagcgagg ggaggtgct gaggaaaacg    3240
gcacacagag tggacttgat tgccaaatac atcgggggc tgagagagca agaaaagagg    3300
atcaagtgtc tggaatcaca ggccaactac tgtatgctcc tcttgtcctc tatgacggat    3360
acactggctc caggaggcac ctactcaagc tctcagaact gtgggttgcag gagtcagcca    3420
```

-continued

```
gcctctgcta gagacaggga gtacctagag tctggcttgc caccctctga cacctgaaat    3480
ggagaaacca cttgctctag agccccagac ctggccacat cgagttttg gggcacatca    3540 accttccccc actcccagca gccccaagaa atggtcttca aggccttgct acagatcact    3600
tcttggacat ccccttcctaa gagaatgaaa ctcatgtctt tggcatctat tcgggagcct   3660
cagaagtatc ctctccagca gggcaagatt tttcatgtcc cactaaagct ttcactggct    3720
tggactggac agctggatct ggccaagtcc tacataggac accatctgcc tggatggggc    3780
tatttaggtc taaccctgt cttaccctga gttcctaaga agccaacctc ttaaacacta    3840
ggtttctttc tgaccctga cccactcatt agctgaccag ctcctagagg gcaggactca     3900
gatctattgt aattacctcc catctttcac cccccacagc attatctgtc tgatcattct    3960
ggcagaaacc ccaagatatt gctcaagggt acccaatgct actttacttt ctataaagcc    4020
tgtagaccac ctcaaatcag ctaaactggg ccacaatggt ggctaaacgg gacatttcaa    4080
acacccgggg aatatggagg attgtctgac ctagtgaaag gcatctccgt tccttccact    4140
gctcctcaaa ttaaatgacc atccaggtcc tttttagagg aactcagaga atggggacta    4200
cagaggctgg ggcagacctg ggtcttagca ggtctagcta acttggtcca agtccctggc    4260
ctccacagga aacattcgct catgcatcct ccctgcatcc ttctcttctt ctctggctca    4320
gcttcagtgg aatgacccag catcagctgt gtcttacaca cacaagtcct ggagacacag    4380
ccagacacca accatatgct gcttcacaac tcatcctctt cctataacct gtggtctgta    4440
caggcccagt gctgggctg cattggtttc tgggggtggg ggtgggggtg ggttgtgcag    4500
attatgctca ttcactacca tcaggggcac aaggctgaac acagctaaga gcccagtccc    4560
tctgggtagt ttcatcagtg acaaatgtaa atgaccatgg caaacctt              4608
```

<210> SEQ ID NO 4
<211> LENGTH: 1158
<212> TYPE: PRT
<213> ORGANISM: Mus musculus
<220> FEATURE:
<223> OTHER INFORMATION: mouse betaTRP (TRPM5) calcium channel

<400> SEQUENCE: 4

```
Met Gln Thr Thr Gln Ser Ser Cys Pro Gly Ser Pro Pro Asp Thr Glu
 1               5                  10                  15

Asp Gly Trp Glu Pro Ile Leu Cys Arg Gly Glu Ile Asn Phe Gly Gly
                20                  25                  30

Ser Gly Lys Lys Arg Gly Lys Phe Val Lys Val Pro Ser Ser Val Ala
            35                  40                  45

Pro Ser Val Leu Phe Glu Leu Leu Leu Thr Glu Trp His Leu Pro Ala
        50                  55                  60

Pro Asn Leu Val Val Ser Leu Val Gly Glu Glu Arg Pro Leu Ala Met
    65                  70                  75                  80

Lys Ser Trp Leu Arg Asp Val Leu Arg Lys Gly Leu Val Lys Ala Ala
                85                  90                  95

Gln Ser Thr Gly Ala Trp Ile Leu Thr Ser Ala Leu His Val Gly Leu
            100                 105                 110

Ala Arg His Val Gly Gln Ala Val Arg Asp His Ser Leu Ala Ser Thr
        115                 120                 125

Ser Thr Lys Ile Arg Val Val Ala Ile Gly Met Ala Ser Leu Asp Arg
    130                 135                 140

Ile Leu His Arg Gln Leu Leu Asp Gly Val His Gln Lys Glu Asp Thr
```

```
145                 150                 155                 160
Pro Ile His Tyr Pro Ala Asp Glu Gly Asn Ile Gln Gly Pro Leu Cys
                165                 170                 175

Pro Leu Asp Ser Asn Leu Ser His Phe Ile Leu Val Glu Ser Gly Ala
            180                 185                 190

Leu Gly Ser Gly Asn Asp Gly Leu Thr Glu Leu Gln Leu Ser Leu Glu
            195                 200                 205

Lys His Ile Ser Gln Gln Arg Thr Gly Tyr Gly Thr Ser Cys Ile
            210                 215                 220

Gln Ile Pro Val Leu Cys Leu Val Asn Gly Asp Pro Asn Thr Leu
225                 230                 235                 240

Glu Arg Ile Ser Arg Ala Val Glu Gln Ala Pro Trp Leu Ile Leu
                245                 250                 255

Ala Gly Ser Gly Gly Ile Ala Asp Val Leu Ala Leu Val Ser Gln
            260                 265                 270

Pro His Leu Leu Val Pro Gln Val Ala Glu Lys Gln Phe Arg Glu Lys
            275                 280                 285

Phe Pro Ser Glu Cys Phe Ser Trp Glu Ala Ile Val His Trp Thr Glu
290                 295                 300

Leu Leu Gln Asn Ile Ala Ala His Pro His Leu Leu Thr Val Tyr Asp
305                 310                 315                 320

Phe Glu Gln Glu Gly Ser Asp Leu Asp Thr Val Ile Leu Lys Ala
            325                 330                 335

Leu Val Lys Ala Cys Lys Ser His Ser Gln Glu Ala Gln Asp Tyr Leu
            340                 345                 350

Asp Glu Leu Lys Leu Ala Val Ala Trp Asp Arg Val Asp Ile Ala Lys
            355                 360                 365

Ser Glu Ile Phe Asn Gly Asp Val Glu Trp Lys Ser Cys Asp Leu Glu
            370                 375                 380

Glu Val Met Thr Asp Ala Leu Val Ser Asn Lys Pro Asp Phe Val Arg
385                 390                 395                 400

Leu Phe Val Asp Ser Gly Ala Asp Met Ala Glu Phe Leu Thr Tyr Gly
                405                 410                 415

Arg Leu Gln Gln Leu Tyr His Ser Val Ser Pro Lys Ser Leu Leu Phe
            420                 425                 430

Glu Leu Leu Gln Arg Lys His Glu Glu Gly Arg Leu Thr Leu Ala Gly
            435                 440                 445

Leu Gly Ala Gln Gln Ala Arg Glu Leu Pro Ile Gly Leu Pro Ala Phe
            450                 455                 460

Ser Leu His Glu Val Ser Arg Val Leu Lys Asp Phe Leu His Asp Ala
465                 470                 475                 480

Cys Arg Gly Phe Tyr Gln Asp Gly Arg Arg Met Glu Arg Gly Pro
                485                 490                 495

Pro Lys Arg Pro Ala Gly Gln Lys Trp Leu Pro Asp Leu Ser Arg Lys
            500                 505                 510

Ser Glu Asp Pro Trp Arg Asp Leu Phe Leu Trp Ala Val Leu Gln Asn
            515                 520                 525

Arg Tyr Glu Met Ala Thr Tyr Phe Trp Ala Met Gly Arg Glu Gly Val
            530                 535                 540

Ala Ala Ala Leu Ala Ala Cys Lys Ile Ile Lys Glu Met Ser His Leu
545                 550                 555                 560

Glu Lys Glu Ala Glu Val Ala Arg Thr Met Arg Glu Ala Lys Tyr Glu
                565                 570                 575
```

-continued

```
Gln Leu Ala Leu Asp Leu Phe Ser Glu Cys Tyr Gly Asn Ser Glu Asp
            580                 585                 590

Arg Ala Phe Ala Leu Leu Val Arg Arg Asn His Ser Trp Ser Arg Thr
        595                 600                 605

Thr Cys Leu His Leu Ala Thr Glu Ala Asp Ala Lys Ala Phe Phe Ala
    610                 615                 620

His Asp Gly Val Gln Ala Phe Leu Thr Lys Ile Trp Trp Gly Asp Met
625                 630                 635                 640

Ala Thr Gly Thr Pro Ile Leu Arg Leu Leu Gly Ala Phe Thr Cys Pro
                645                 650                 655

Ala Leu Ile Tyr Thr Asn Leu Ile Ser Phe Ser Glu Asp Ala Pro Gln
            660                 665                 670

Arg Met Asp Leu Glu Asp Leu Gln Glu Pro Asp Ser Leu Asp Met Glu
        675                 680                 685

Lys Ser Phe Leu Cys Ser Arg Gly Gly Gln Leu Glu Lys Leu Thr Glu
    690                 695                 700

Ala Pro Arg Ala Pro Gly Asp Leu Gly Pro Gln Ala Ala Phe Leu Leu
705                 710                 715                 720

Thr Arg Trp Arg Lys Phe Trp Gly Ala Pro Val Thr Val Phe Leu Gly
                725                 730                 735

Asn Val Val Met Tyr Phe Ala Phe Leu Phe Leu Phe Thr Tyr Val Leu
            740                 745                 750

Leu Val Asp Phe Arg Pro Pro Gln Gly Pro Ser Gly Ser Glu Val
        755                 760                 765

Thr Leu Tyr Phe Trp Val Phe Thr Leu Val Leu Glu Glu Ile Arg Gln
    770                 775                 780

Gly Phe Phe Thr Asp Glu Asp Thr His Leu Val Lys Lys Phe Thr Leu
785                 790                 795                 800

Tyr Val Glu Asp Asn Trp Asn Lys Cys Asp Met Val Ala Ile Phe Leu
                805                 810                 815

Phe Ile Val Gly Val Thr Cys Arg Met Val Pro Ser Val Phe Glu Ala
            820                 825                 830

Gly Arg Thr Val Leu Ala Ile Asp Phe Met Val Phe Thr Leu Arg Leu
        835                 840                 845

Ile His Ile Phe Ala Ile His Lys Gln Leu Gly Pro Lys Ile Ile Ile
    850                 855                 860

Val Glu Arg Met Met Lys Asp Val Phe Phe Leu Phe Phe Leu Ser
865                 870                 875                 880

Val Trp Leu Val Ala Tyr Gly Val Thr Thr Gln Ala Leu Leu His Pro
                885                 890                 895

His Asp Gly Arg Leu Glu Trp Ile Phe Arg Arg Val Leu Tyr Arg Pro
            900                 905                 910

Tyr Leu Gln Ile Phe Gly Gln Ile Pro Leu Asp Glu Ile Asp Glu Ala
        915                 920                 925

Arg Val Asn Cys Ser Leu His Pro Leu Leu Glu Ser Ser Ala Ser
    930                 935                 940

Cys Pro Asn Leu Tyr Ala Asn Trp Leu Val Ile Leu Leu Leu Val Thr
945                 950                 955                 960

Phe Leu Leu Val Thr Asn Val Leu Leu Met Asn Leu Leu Ile Ala Met
                965                 970                 975

Phe Ser Tyr Thr Phe Gln Val Val Gln Gly Asn Ala Asp Met Phe Trp
            980                 985                 990
```

```
Lys Phe Gln Arg Tyr His Leu Ile Val Glu Tyr His Gly Arg Pro Ala
            995                 1000                1005

Leu Ala Pro Pro Phe Ile Leu Leu Ser His Leu Ser Leu Val Leu Lys
        1010                1015                1020

Gln Val Phe Arg Lys Glu Ala Gln His Lys Arg Gln His Leu Glu Arg
1025                1030                1035                1040

Asp Leu Pro Asp Pro Leu Asp Gln Lys Ile Ile Thr Trp Glu Thr Val
            1045                1050                1055

Gln Lys Glu Asn Phe Leu Ser Thr Met Glu Lys Arg Arg Arg Asp Ser
        1060                1065                1070

Glu Gly Glu Val Leu Arg Lys Thr Ala His Arg Val Asp Leu Ile Ala
        1075                1080                1085

Lys Tyr Ile Gly Gly Leu Arg Glu Gln Glu Lys Arg Ile Lys Cys Leu
        1090                1095                1100

Glu Ser Gln Ala Asn Tyr Cys Met Leu Leu Leu Ser Ser Met Thr Asp
1105                1110                1115                1120

Thr Leu Ala Pro Gly Gly Thr Tyr Ser Ser Ser Gln Asn Cys Gly Cys
            1125                1130                1135

Arg Ser Gln Pro Ala Ser Ala Arg Asp Arg Glu Tyr Leu Glu Ser Gly
        1140                1145                1150

Leu Pro Pro Ser Asp Thr
        1155

<210> SEQ ID NO 5
<211> LENGTH: 3468
<212> TYPE: DNA
<213> ORGANISM: Rattus sp.
<220> FEATURE:
<223> OTHER INFORMATION: rat betaTRP calcium channel

<400> SEQUENCE: 5
atgccgatgg cccagagctc ttgtcctgga agcccccag atactgggga tggatgggag      60
ccagtcctat gcaagggaga ggtcaacttc ggagggtctg ggaaaaagcg aagcaagttt    120
gtgaaggtgc caagcaatgt ggcccccctcc atgctctttg aactcctgct caccgagtgg    180
cacctgccag cccccaacct ggtggtgtcc ctggtgggcg aggaacggct ttttgctatg    240
aagtcctggc ttcgggatgt cttgcgcaag gggctggtga agcagctca gagcacaggt    300 gcctggatcc tgaccagtgc cctccatgtg ggcctggcac gccatgttgg acaggctgta    360
cgtgatcact ctctggctag cacgtccacc aaggtccgtg tggtggccat cggaatggcc    420
tctctggacc gaatccttca ccgccaactt ctagatggtg tccaggagga tactcccatc    480
cactacccag cagatgaggg cagcactcag ggacccctct gccctctgga cagcaatctc    540
tcccacttca tcctcgtgga gccaggcacc cttgggagtg ggaacgacgg actggcagag    600
ctgcagctga gcctggagaa gcacatctct cagcagagga caggttatgg gggtaccagc    660
agcatccaga tacctgtcct ttgcttgcta gtcaatggtg accccagcac cctagagagg    720
atgtccaggg cagtggagca ggctgcccca tggctgatcc tggcaggttc tgggggcatt    780
gctgatgtac tcgctgccct ggtgggccag cctcatctcc tggtgcccca ggtgaccgag    840
aagcagttca gagagaaatt cccaagcgag tgtttctctt gggaagccat tgtacactgg    900
acagagctgc tacagaacat tgctgcacac ccccacctgc tcacagtgta cgactttgag    960
caggagggtt ccgaggacct ggacaccgtc atcctcaagg cacttgtgaa agcctgcaag   1020
agtcacagcc gagacgcaca agactaccta gatgagctca agttagcagt ggcctgggat   1080
```

```
cgcgtggaca ttgccaagag tgaaatcttc aatggggacg tggagtggaa gtcctgtgac   1140
ttggaagagg tgatgacaga tgccctagtg agcaacaagc ctgacttcgt gcgcctcttt   1200
gtggacagtg gtgctgacat ggccgagttc ttgacctatg gcggctgca gcagctttac    1260 cactctgtgt cccccaagag cctcctcttt gaactgctgg agcgtaagca tgaggagggt   1320
cggctgacac tggctggcct gggtgcccag cagacccggg agctgcccgt tggtctgcct   1380
gccttttcac tccatgaggt ctcccgagtt ctcaaagatt tcctgcatga cgcctgccgt   1440
ggcttctacc aggatgggcg caggatggag gagagagggc cacccaagcg gcctgcaggc   1500
cagaaatggc tgccggacct cagtcggaag agtgaagacc catggaggga cctgttcctt   1560
tgggctgtgc tgcagaaccg ttatgagatg ccacatact tctgggccat gggccgggag    1620
ggtgtggctg ctgctctggc ggcctgcaag atcatcaagg aaatgtccca cctggagaaa   1680
gaggcagagg tggcccgcac tatgcgtgag gccaagtatg agcagctggc cctcgatctt   1740
ttctcagagt gctacagcaa cagtgaggac cgtgcctttg ccctgttggt gcgcaggaac   1800
cacagctgga gcaggaccac ctgcctgcac ctggccactg aggccgatgc caaggccttc   1860
tttgcccatg atggtgtgca agcattcctg acgaagatct ggtggggaga catggccaca   1920
ggcacaccca tcttacgact tctgggtgcc ttcacctgcc cagccctcat ctacacaaat   1980
ctcatctcct tcagtgagga tgccccgcag aggatggacc tggaagatct gcaggagcca   2040
gacagtttgg atatggaaaa gagcttcctg tgcagccatg gtggccagtt ggagaagtta   2100
acagaggcgc caaggctcc tggcgatcta ggcccacaag ctgccttcct gctcacacgg    2160
tggaggaagt tctggggcgc tcctgtgact gtgttcttgg ggaatgtggt catgtacttt   2220
gcattcctct tcctattctc ctacgtcctg ctggtggatt tcaggccacc accccagggg   2280
ccatctgggt cggaagttac cctgtatttc tgggtcttca cactggtgct ggaggaaatc   2340
cgacagggat tcttcacaaa cgaggacacc cgtctggtga agaagttcac tctgtacgta   2400
gaagacaact ggaacaaatg tgacatggtg gccatcttcc tgttcattgt tggtgtcacc   2460
tgtaggatgg tgccctccgt gtttgaggct ggccggactg ttctggccat tgacttcatg   2520
gtgttcacac ttcggctcat ccacatcttt gctattcaca gcagctggg tcctaagatc   2580 atcattgtag agcggatgat gaaagatgtc ttcttcttcc tcttcttcct gagcgtgtgg   2640
ctcgtggcct atggcgtgac cactcaggcc ctgctgcacc ccacgatgg ccgtctggag    2700 tggattttcc gccgtgtgct ctacaggcct tacctgcaga tctttgggca aatccctctg   2760
gatgaaattg atgaggcccg tgtgaactgc tctcttcacc cgttgctgct ggacagctca   2820
gcttcctgcc ctaatctcta tgccaactgg ctggtcattc tcctgctggt taccttcctc   2880
ctcgtcacta atgtgctact tatgaacctt ctgatcgcca tgttcagcta cactttccag   2940
gtggtgcagg gcaatgcaga catgttctgg aagtttcaac gctaccacct catcgttgaa   3000
taccacggaa ggccggctct ggccccgccc ttcatcctgc tcagccacct gagcctggtg   3060
ctcaagcagg tcttcaggaa ggaagcccag cacaaacagc aacacctgga gagagacttg   3120
cctgaccccg tggaccagaa gatcattacc tgggaaacag ttcaaaagga gaacttcctg   3180
agtaccatgg agaaacggag gagggacagt gaggaggagg tgctgaggaa acggcacac    3240 agggtggact tgattgccaa atacatcggg gtctgagag agcaagaaaa gaggatcaag    3300
tgtctggagt cacaggcaaa ctactgtatg ctcctcttgt cctccatgac tgacacactg   3360
gctcctggag gcacctactc aagttctcaa aactgtggtc gcaggagtca gccagcctct   3420
gctagagaca gggagtacct agaggctggc ttgccacact cagacacc                3468
```

<210> SEQ ID NO 6
<211> LENGTH: 1156
<212> TYPE: PRT
<213> ORGANISM: Rattus sp.
<220> FEATURE:
<223> OTHER INFORMATION: rat betaTRP calcium channel

<400> SEQUENCE: 6

```
Met Pro Met Ala Gln Ser Ser Cys Pro Gly Ser Pro Asp Thr Gly
 1               5                  10                  15

Asp Gly Trp Glu Pro Val Leu Cys Lys Gly Glu Val Asn Phe Gly Gly
            20                  25                  30

Ser Gly Lys Lys Arg Ser Lys Phe Val Lys Val Pro Ser Asn Val Ala
        35                  40                  45

Pro Ser Met Leu Phe Glu Leu Leu Thr Glu Trp His Leu Pro Ala
 50                  55                  60

Pro Asn Leu Val Val Ser Leu Val Gly Glu Arg Leu Phe Ala Met
 65                  70                  75                  80

Lys Ser Trp Leu Arg Asp Val Leu Arg Lys Gly Leu Val Lys Ala Ala
            85                  90                  95

Gln Ser Thr Gly Ala Trp Ile Leu Thr Ser Ala Leu His Val Gly Leu
            100                 105                 110

Ala Arg His Val Gly Gln Ala Val Arg Asp His Ser Leu Ala Ser Thr
        115                 120                 125

Ser Thr Lys Val Arg Val Ala Ile Gly Met Ala Ser Leu Asp Arg
    130                 135                 140

Ile Leu His Arg Gln Leu Leu Asp Gly Val Gln Glu Asp Thr Pro Ile
145                 150                 155                 160

His Tyr Pro Ala Asp Glu Gly Ser Thr Gln Gly Pro Leu Cys Pro Leu
                165                 170                 175

Asp Ser Asn Leu Ser His Phe Ile Leu Val Glu Pro Gly Thr Leu Gly
                180                 185                 190

Ser Gly Asn Asp Gly Leu Ala Glu Leu Gln Leu Ser Leu Glu Lys His
            195                 200                 205

Ile Ser Gln Gln Arg Thr Gly Tyr Gly Gly Thr Ser Ser Ile Gln Ile
    210                 215                 220

Pro Val Leu Cys Leu Leu Val Asn Gly Asp Pro Ser Thr Leu Glu Arg
225                 230                 235                 240

Met Ser Arg Ala Val Glu Gln Ala Ala Pro Trp Leu Ile Leu Ala Gly
                245                 250                 255

Ser Gly Gly Ile Ala Asp Val Leu Ala Ala Leu Val Gly Gln Pro His
            260                 265                 270

Leu Leu Val Pro Gln Val Thr Glu Lys Gln Phe Arg Glu Lys Phe Pro
        275                 280                 285

Ser Glu Cys Phe Ser Trp Glu Ala Ile His Trp Thr Glu Leu Leu
    290                 295                 300

Gln Asn Ile Ala Ala His Pro His Leu Leu Thr Val Tyr Asp Phe Glu
305                 310                 315                 320

Gln Glu Gly Ser Glu Asp Leu Asp Thr Val Ile Leu Lys Ala Leu Val
                325                 330                 335

Lys Ala Cys Lys Ser His Ser Arg Asp Ala Gln Asp Tyr Leu Asp Glu
            340                 345                 350

Leu Lys Leu Ala Val Ala Trp Asp Arg Val Asp Ile Ala Lys Ser Glu
        355                 360                 365
```

```
Ile Phe Asn Gly Asp Val Glu Trp Lys Ser Cys Asp Leu Glu Glu Val
    370                 375                 380

Met Thr Asp Ala Leu Val Ser Asn Lys Pro Asp Phe Val Arg Leu Phe
385                 390                 395                 400

Val Asp Ser Gly Ala Asp Met Ala Glu Phe Leu Thr Tyr Gly Arg Leu
                405                 410                 415

Gln Gln Leu Tyr His Ser Val Ser Pro Lys Ser Leu Leu Phe Glu Leu
            420                 425                 430

Leu Glu Arg Lys His Glu Gly Arg Leu Thr Leu Ala Gly Leu Gly
        435                 440                 445

Ala Gln Gln Thr Arg Glu Leu Pro Val Gly Leu Pro Ala Phe Ser Leu
450                 455                 460

His Glu Val Ser Arg Val Leu Lys Asp Phe Leu His Asp Ala Cys Arg
465                 470                 475                 480

Gly Phe Tyr Gln Asp Gly Arg Arg Met Glu Glu Arg Gly Pro Pro Lys
                485                 490                 495

Arg Pro Ala Gly Gln Lys Trp Leu Pro Asp Leu Ser Arg Lys Ser Glu
                500                 505                 510

Asp Pro Trp Arg Asp Leu Phe Leu Trp Ala Val Leu Gln Asn Arg Tyr
            515                 520                 525

Glu Met Ala Thr Tyr Phe Trp Ala Met Gly Arg Glu Gly Val Ala Ala
            530                 535                 540

Ala Leu Ala Ala Cys Lys Ile Ile Lys Glu Met Ser His Leu Glu Lys
545                 550                 555                 560

Glu Ala Glu Val Ala Arg Thr Met Arg Glu Ala Lys Tyr Glu Gln Leu
                565                 570                 575

Ala Leu Asp Leu Phe Ser Glu Cys Tyr Ser Asn Ser Glu Asp Arg Ala
            580                 585                 590

Phe Ala Leu Leu Val Arg Arg Asn His Ser Trp Ser Arg Thr Thr Cys
595                 600                 605

Leu His Leu Ala Thr Glu Ala Asp Ala Lys Ala Phe Phe Ala His Asp
    610                 615                 620

Gly Val Gln Ala Phe Leu Thr Lys Ile Trp Trp Gly Asp Met Ala Thr
625                 630                 635                 640

Gly Thr Pro Ile Leu Arg Leu Leu Gly Ala Phe Thr Cys Pro Ala Leu
                645                 650                 655

Ile Tyr Thr Asn Leu Ile Ser Phe Ser Glu Asp Ala Pro Gln Arg Met
                660                 665                 670

Asp Leu Glu Asp Leu Gln Glu Pro Asp Ser Leu Asp Met Glu Lys Ser
            675                 680                 685

Phe Leu Cys Ser His Gly Gly Gln Leu Glu Lys Leu Thr Glu Ala Pro
    690                 695                 700

Arg Ala Pro Gly Asp Leu Gly Pro Gln Ala Ala Phe Leu Leu Thr Arg
705                 710                 715                 720

Trp Arg Lys Phe Trp Gly Ala Pro Val Thr Val Phe Leu Gly Asn Val
                725                 730                 735

Val Met Tyr Phe Ala Phe Leu Phe Leu Phe Ser Tyr Val Leu Leu Val
            740                 745                 750

Asp Phe Arg Pro Pro Gln Gly Pro Ser Gly Ser Glu Val Thr Leu
            755                 760                 765

Tyr Phe Trp Val Phe Thr Leu Val Leu Glu Glu Ile Arg Gln Gly Phe
770                 775                 780
```

```
Phe Thr Asn Glu Asp Thr Arg Leu Val Lys Lys Phe Thr Leu Tyr Val
785                 790                 795                 800

Glu Asp Asn Trp Asn Lys Cys Asp Met Val Ala Ile Phe Leu Phe Ile
            805                 810                 815

Val Gly Val Thr Cys Arg Met Val Pro Ser Val Phe Glu Ala Gly Arg
            820                 825                 830

Thr Val Leu Ala Ile Asp Phe Met Val Phe Thr Leu Arg Leu Ile His
            835                 840                 845

Ile Phe Ala Ile His Lys Gln Leu Gly Pro Lys Ile Ile Val Glu
850                 855                 860

Arg Met Met Lys Asp Val Phe Phe Leu Phe Leu Ser Val Trp
865                 870                 875                 880

Leu Val Ala Tyr Gly Val Thr Thr Gln Ala Leu Leu His Pro His Asp
            885                 890                 895

Gly Arg Leu Glu Trp Ile Phe Arg Arg Val Leu Tyr Arg Pro Tyr Leu
            900                 905                 910

Gln Ile Phe Gly Gln Ile Pro Leu Asp Glu Ile Asp Glu Ala Arg Val
            915                 920                 925

Asn Cys Ser Leu His Pro Leu Leu Asp Ser Ala Ser Cys Pro
            930                 935                 940

Asn Leu Tyr Ala Asn Trp Leu Val Ile Leu Leu Val Thr Phe Leu
945                 950                 955                 960

Leu Val Thr Asn Val Leu Leu Met Asn Leu Leu Ile Ala Met Phe Ser
            965                 970                 975

Tyr Thr Phe Gln Val Val Gln Gly Asn Ala Asp Met Phe Trp Lys Phe
            980                 985                 990

Gln Arg Tyr His Leu Ile Val Glu Tyr His Gly Arg Pro Ala Leu Ala
            995                 1000                1005

Pro Pro Phe Ile Leu Leu Ser His Leu Ser Leu Val Leu Lys Gln Val
            1010                1015                1020

Phe Arg Lys Glu Ala Gln His Lys Gln Gln His Leu Glu Arg Asp Leu
1025                1030                1035                1040

Pro Asp Pro Val Asp Gln Lys Ile Ile Thr Trp Glu Thr Val Gln Lys
            1045                1050                1055

Glu Asn Phe Leu Ser Thr Met Glu Lys Arg Arg Arg Asp Ser Glu Glu
            1060                1065                1070

Glu Val Leu Arg Lys Thr Ala His Arg Val Asp Leu Ile Ala Lys Tyr
            1075                1080                1085

Ile Gly Gly Leu Arg Glu Gln Glu Lys Arg Ile Lys Cys Leu Glu Ser
            1090                1095                1100

Gln Ala Asn Tyr Cys Met Leu Leu Leu Ser Ser Met Thr Asp Thr Leu
1105                1110                1115                1120

Ala Pro Gly Gly Thr Tyr Ser Ser Ser Gln Asn Cys Gly Arg Arg Ser
            1125                1130                1135

Gln Pro Ala Ser Ala Arg Asp Arg Glu Tyr Leu Glu Ala Gly Leu Pro
            1140                1145                1150

His Ser Asp Thr
            1155

<210> SEQ ID NO 7
<211> LENGTH: 1165
<212> TYPE: PRT
<213> ORGANISM: Homo sapiens
<220> FEATURE:
<223> OTHER INFORMATION: human betaTRP (MBX) calcium channel
```

<400> SEQUENCE: 7

```
Met Gln Asp Val Gln Gly Pro Arg Pro Gly Ser Pro Gly Asp Ala Glu
 1               5                  10                  15

Asp Arg Arg Glu Leu Gly Leu His Arg Gly Glu Val Asn Asn Gly Gly
             20                  25                  30

Ser Gly Lys Lys Arg Gly Lys Asn Val Arg Val Pro Ser Gly Val Ala
         35                  40                  45

Pro Ser Val Leu Asn Asp Leu Leu Ala Glu Trp His Leu Pro Ala
 50                  55                  60

Pro Asn Leu Val Val Ser Leu Val Gly Glu Glu Gln Pro Phe Ala Met
 65                  70                  75                  80

Lys Ser Trp Leu Arg Asp Val Leu Arg Lys Gly Leu Val Lys Ala Ala
                 85                  90                  95

Gln Ser Thr Gly Ala Trp Ile Leu Thr Ser Ala Leu Arg Val Gly Leu
            100                 105                 110

Ala Arg His Val Gly Gln Ala Val Arg Asp His Ser Leu Ala Ser Thr
            115                 120                 125

Ser Thr Lys Val Arg Val Ala Val Gly Met Ala Ser Leu Gly Arg
130                 135                 140

Val Leu His Arg Arg Ile Leu Glu Glu Ala Gln Glu Asp Asn Pro Val
145                 150                 155                 160

His Tyr Pro Glu Asp Gly Gly Ser Gln Gly Pro Leu Cys Ser Leu
                165                 170                 175

Asp Ser Asn Leu Ser His Phe Ile Leu Val Glu Pro Gly Pro Pro Gly
                180                 185                 190

Lys Gly Asp Gly Leu Thr Glu Leu Arg Leu Arg Leu Glu Lys His Ile
            195                 200                 205

Ser Glu Gln Arg Ala Gly Tyr Gly Gly Thr Gly Ser Ile Glu Ile Pro
210                 215                 220

Val Leu Cys Leu Leu Val Asn Gly Asp Pro Asn Thr Leu Glu Arg Ile
225                 230                 235                 240

Ser Arg Ala Val Glu Gln Ala Ala Pro Trp Leu Ile Leu Val Gly Ser
                245                 250                 255

Gly Gly Ile Ala Asp Val Leu Ala Ala Leu Val Asn Gln Pro His Leu
            260                 265                 270

Leu Val Pro Lys Val Ala Glu Lys Gln Asn Lys Glu Lys Phe Pro Ser
            275                 280                 285

Lys His Phe Ser Trp Glu Asp Ile Val Arg Trp Thr Lys Leu Leu Gln
            290                 295                 300

Asn Ile Thr Ser His Gln His Leu Leu Thr Val Tyr Asp Phe Glu Gln
305                 310                 315                 320

Glu Gly Ser Glu Glu Leu Asp Thr Val Ile Leu Lys Ala Leu Val Lys
                325                 330                 335

Ala Cys Lys Ser His Ser Gln Glu Pro Gln Asp Tyr Leu Asp Glu Leu
            340                 345                 350

Lys Leu Ala Val Ala Trp Asp Arg Val Asp Ile Ala Lys Ser Glu Ile
            355                 360                 365

Phe Asn Gly Asp Val Glu Trp Lys Ser Cys Asp Leu Glu Glu Val Met
            370                 375                 380

Val Asp Ala Leu Val Ser Asn Lys Pro Glu Asn Val Arg Leu Asn Val
385                 390                 395                 400

Asp Asn Gly Ala Asp Val Ala Asp Phe Leu Thr Tyr Gly Arg Leu Gln
```

-continued

```
                405                 410                 415
Glu Leu Tyr Arg Ser Val Ser Arg Lys Ser Leu Leu Phe Asp Leu Leu
            420                 425                 430
Gln Arg Lys Gln Glu Glu Ala Arg Leu Thr Leu Ala Gly Leu Gly Thr
        435                 440                 445
Gln Gln Ala Arg Glu Pro Pro Ala Gly Pro Pro Ala Phe Ser Leu His
    450                 455                 460
Glu Val Ser Arg Val Leu Lys Asp Phe Leu Gln Asp Ala Cys Arg Gly
465                 470                 475                 480
Phe Tyr Gln Asp Gly Arg Pro Gly Asp Arg Arg Ala Glu Lys Gly
                485                 490                 495
Pro Ala Lys Arg Pro Thr Gly Gln Lys Trp Leu Leu Asp Leu Asn Gln
            500                 505                 510
Lys Ser Glu Asn Pro Trp Arg Asp Leu Phe Leu Trp Ala Val Leu Gln
        515                 520                 525
Asn Arg His Glu Met Ala Thr Tyr Phe Trp Ala Met Gly Gln Glu Gly
    530                 535                 540
Val Ala Ala Leu Ala Ala Cys Lys Ile Leu Lys Glu Met Ser His
545                 550                 555                 560
Leu Glu Thr Glu Ala Glu Ala Arg Ala Thr Arg Glu Ala Lys Tyr
                565                 570                 575
Glu Arg Leu Ala Leu Asp Leu Phe Ser Glu Cys Tyr Ser Asn Ser Glu
            580                 585                 590
Ala Arg Ala Phe Ala Leu Leu Val Arg Arg Asn Arg Cys Trp Ser Lys
        595                 600                 605
Thr Thr Cys Leu His Leu Ala Thr Glu Ala Asp Ala Lys Ala Phe Asn
    610                 615                 620
Ala His Asp Gly Val Gln Ala Phe Leu Thr Arg Ile Trp Trp Gly Asp
625                 630                 635                 640
Met Ala Ala Gly Thr Pro Ile Leu Arg Leu Leu Gly Ala Phe Leu Cys
                645                 650                 655
Pro Ala Leu Val Tyr Thr Asn Leu Ile Thr Phe Ser Glu Glu Ala Pro
            660                 665                 670
Leu Arg Thr Gly Leu Glu Asp Leu Gln Asp Leu Asp Ser Leu Asp Thr
        675                 680                 685
Glu Lys Ser Pro Leu Tyr Gly Leu Gln Ser Arg Val Glu Glu Leu Val
    690                 695                 700
Glu Ala Pro Arg Ala Gln Gly Asp Arg Gly Pro Arg Ala Val Phe Leu
705                 710                 715                 720
Leu Thr Arg Trp Arg Lys Phe Trp Gly Ala Pro Val Thr Val Phe Leu
                725                 730                 735
Gly Asn Val Val Met Tyr Phe Ala Phe Leu Phe Leu Phe Thr Tyr Val
            740                 745                 750
Leu Leu Val Asp Phe Arg Pro Pro Gln Gly Pro Ser Gly Pro Glu
        755                 760                 765
Val Thr Leu Tyr Phe Trp Val Asn Thr Leu Val Leu Glu Glu Ile Arg
    770                 775                 780
Gln Gly Phe Phe Thr Asp Glu Asp Thr His Leu Val Lys Lys Phe Thr
785                 790                 795                 800
Leu Tyr Val Gly Asp Asn Trp Asn Lys Cys Asp Met Val Ala Ile Phe
                805                 810                 815
Leu Phe Ile Val Gly Val Thr Cys Arg Met Leu Pro Ser Ala Asn Glu
            820                 825                 830
```

```
Ala Gly Arg Thr Val Leu Ala Met Asp Phe Met Val Phe Thr Leu Arg
        835                 840                 845

Leu Ile His Ile Asn Ala Ile His Lys Gln Leu Gly Pro Lys Ile Ile
        850                 855                 860

Val Val Glu Arg Met Met Lys Asp Val Phe Phe Leu Phe Asn Leu
865                 870                 875                 880

Ser Val Trp Leu Val Ala Tyr Gly Val Thr Thr Gln Ala Leu Leu His
                885                 890                 895

Pro His Asp Gly Arg Leu Glu Trp Ile Phe Arg Arg Val Leu Tyr Arg
                900                 905                 910

Pro Tyr Leu Gln Ile Phe Gly Gln Ile Pro Leu Asp Glu Ile Asp Glu
                915                 920                 925

Ala Arg Val Asn Cys Ser Thr His Pro Leu Leu Glu Asp Ser Pro
                930                 935                 940

Ser Cys Pro Ser Leu Tyr Ala Asn Trp Leu Val Ile Leu Leu Leu Val
945                 950                 955                 960

Thr Phe Leu Leu Val Thr Asn Val Leu Leu Met Asn Leu Leu Ile Ala
                965                 970                 975

Met Phe Ser Tyr Thr Phe Gln Val Val Gln Gly Asn Ala Asp Met Phe
                980                 985                 990

Trp Lys Phe Gln Arg Tyr Asn Leu Ile Val Glu Tyr His Glu Arg Pro
                995                 1000                1005

Ala Leu Ala Pro Pro Phe Ile Leu Leu Ser His Leu Ser Leu Thr Leu
        1010                1015                1020

Arg Arg Val Phe Lys Lys Glu Ala Glu His Lys Arg Glu His Leu Glu
1025                1030                1035                1040

Arg Asp Leu Pro Asp Pro Leu Asp Gln Lys Val Val Thr Trp Glu Thr
                1045                1050                1055

Val Gln Lys Glu Asn Phe Leu Ser Lys Met Glu Lys Arg Arg Arg Asp
                1060                1065                1070

Ser Glu Gly Glu Val Leu Arg Lys Thr Ala His Arg Val Asp Phe Ile
        1075                1080                1085

Ala Lys Tyr Leu Gly Gly Leu Arg Glu Gln Glu Lys Arg Ile Lys Cys
        1090                1095                1100

Leu Glu Ser Gln Ile Asn Tyr Cys Ser Val Leu Val Ser Ser Val Ala
1105                1110                1115                1120

Asp Val Leu Ala Gln Gly Gly Pro Arg Ser Ser Gln His Cys Gly
                1125                1130                1135

Glu Gly Ser Gln Leu Val Ala Ala Asp His Arg Gly Gly Leu Asp Gly
        1140                1145                1150

Trp Glu Gln Pro Gly Ala Gly Gln Pro Pro Ser Asp Thr
        1155                1160                1165

<210> SEQ ID NO 8
<211> LENGTH: 1168
<212> TYPE: PRT
<213> ORGANISM: Artificial Sequence
<220> FEATURE:
<223> OTHER INFORMATION: Description of Artificial Sequence:consensus
      betaTRP sequence
<220> FEATURE:
<221> NAME/KEY: MOD_RES
<222> LOCATION: (3)
<223> OTHER INFORMATION: Xaa = Met, Thr or Asp
<220> FEATURE:
<221> NAME/KEY: MOD_RES
<222> LOCATION: (4)
```

-continued

```
<223> OTHER INFORMATION: Xaa = Ala, Thr or Val
<220> FEATURE:
<221> NAME/KEY: MOD_RES
<222> LOCATION: (22)
<223> OTHER INFORMATION: Xaa = Val, Ile or Gly
<220> FEATURE:
<221> NAME/KEY: MOD_RES
<222> LOCATION: (46)
<223> OTHER INFORMATION: Xaa = Asn, Ser or Gly
<220> FEATURE:
<221> NAME/KEY: MOD_RES
<222> LOCATION: (156)
<223> OTHER INFORMATION: Xaa = Gln or is absent
<220> FEATURE:
<221> NAME/KEY: MOD_RES
<222> LOCATION: (157)
<223> OTHER INFORMATION: Xaa = Lys or is absent
<220> FEATURE:
<221> NAME/KEY: MOD_RES
<222> LOCATION: (170)
<223> OTHER INFORMATION: Xaa = Ser, Asn or Gly
<220> FEATURE:
<221> NAME/KEY: MOD_RES
<222> LOCATION: (171)
<223> OTHER INFORMATION: Xaa = Thr, Ile or Ser
<220> FEATURE:
<221> NAME/KEY: MOD_RES
<222> LOCATION: (192)
<223> OTHER INFORMATION: Xaa = Thr, Ala or Pro
<220> FEATURE:
<221> NAME/KEY: MOD_RES
<222> LOCATION: (271)
<223> OTHER INFORMATION: Xaa = Gly, Ser or Asn
<220> FEATURE:
<221> NAME/KEY: MOD_RES
<222> LOCATION: (459)
<223> OTHER INFORMATION: Xaa = Val, Ile or Ala
<220> FEATURE:
<221> NAME/KEY: MOD_RES
<222> LOCATION: (490)
<223> OTHER INFORMATION: Xaa = Pro or is absent
<220> FEATURE:
<221> NAME/KEY: MOD_RES
<222> LOCATION: (491)
<223> OTHER INFORMATION: Xaa = Gly or is absent
<220> FEATURE:
<221> NAME/KEY: MOD_RES
<222> LOCATION: (492)
<223> OTHER INFORMATION: Xaa = Asp or is absent
<220> FEATURE:
<221> NAME/KEY: MOD_RES
<222> LOCATION: (493)
<223> OTHER INFORMATION: Xaa = Arg or is absent
<220> FEATURE:
<221> NAME/KEY: MOD_RES
<222> LOCATION: (699)
<223> OTHER INFORMATION: Xaa = His, Arg or Leu
<220> FEATURE:
<221> NAME/KEY: MOD_RES
<222> LOCATION: (1140)
<223> OTHER INFORMATION: Xaa = Arg, Cys or Glu
<220> FEATURE:
<221> NAME/KEY: MOD_RES
<222> LOCATION: (1151)..(1152)
<223> OTHER INFORMATION: Xaa = Gly or is absent
<220> FEATURE:
<221> NAME/KEY: MOD_RES
<222> LOCATION: (1153)
<223> OTHER INFORMATION: Xaa = Leu or is absent
<220> FEATURE:
<221> NAME/KEY: MOD_RES
<222> LOCATION: (1154)
<223> OTHER INFORMATION: Xaa = Asp or is absent
<220> FEATURE:
<221> NAME/KEY: MOD_RES
<222> LOCATION: (1155)
<223> OTHER INFORMATION: Xaa = Gly or is absent
<220> FEATURE:
<221> NAME/KEY: MOD_RES
```

<222> LOCATION: (1156)
<223> OTHER INFORMATION: Xaa = Trp or is absent

<400> SEQUENCE: 8

```
Met Gln Xaa Xaa Gln Ser Ser Cys Pro Gly Ser Pro Pro Asp Thr Glu
 1               5                  10                  15

Asp Gly Trp Glu Pro Xaa Leu Cys Arg Gly Glu Val Asn Phe Gly Gly
            20                  25                  30

Ser Gly Lys Lys Arg Gly Lys Phe Val Lys Val Pro Ser Xaa Val Ala
        35                  40                  45

Pro Ser Val Leu Phe Glu Leu Leu Thr Glu Trp His Leu Pro Ala
50                  55                  60

Pro Asn Leu Val Val Ser Leu Val Gly Glu Glu Arg Pro Phe Ala Met
65                  70                  75                  80

Lys Ser Trp Leu Arg Asp Val Leu Arg Lys Gly Leu Val Lys Ala Ala
                85                  90                  95

Gln Ser Thr Gly Ala Trp Ile Leu Thr Ser Ala Leu His Val Gly Leu
            100                 105                 110

Ala Arg His Val Gly Gln Ala Val Arg Asp His Ser Leu Ala Ser Thr
        115                 120                 125

Ser Thr Lys Val Arg Val Val Ala Ile Gly Met Ala Ser Leu Asp Arg
130                 135                 140

Ile Leu His Arg Gln Leu Leu Asp Gly Val Gln Xaa Xaa Glu Asp Thr
145                 150                 155                 160

Pro Ile His Tyr Pro Ala Asp Glu Gly Xaa Xaa Gln Gly Pro Leu Cys
                165                 170                 175

Pro Leu Asp Ser Asn Leu Ser His Phe Ile Leu Val Glu Pro Gly Xaa
            180                 185                 190

Leu Gly Ser Gly Asn Asp Gly Leu Thr Glu Leu Gln Leu Ser Leu Glu
        195                 200                 205

Lys His Ile Ser Gln Gln Arg Thr Gly Tyr Gly Gly Thr Ser Ser Ile
210                 215                 220

Gln Ile Pro Val Leu Cys Leu Leu Val Asn Gly Asp Pro Asn Thr Leu
225                 230                 235                 240

Glu Arg Ile Ser Arg Ala Val Glu Gln Ala Ala Pro Trp Leu Ile Leu
                245                 250                 255

Ala Gly Ser Gly Gly Ile Ala Asp Val Leu Ala Ala Leu Val Xaa Gln
            260                 265                 270

Pro His Leu Leu Val Pro Gln Val Ala Glu Lys Gln Phe Arg Glu Lys
        275                 280                 285

Phe Pro Ser Glu Cys Phe Ser Trp Glu Ala Ile Val His Trp Thr Glu
290                 295                 300

Leu Leu Gln Asn Ile Ala Ala His Pro His Leu Leu Thr Val Tyr Asp
305                 310                 315                 320

Phe Glu Gln Glu Gly Ser Glu Asp Leu Asp Thr Val Ile Leu Lys Ala
                325                 330                 335

Leu Val Lys Ala Cys Lys Ser His Ser Gln Glu Ala Gln Asp Tyr Leu
            340                 345                 350

Asp Glu Leu Lys Leu Ala Val Ala Trp Asp Arg Val Asp Ile Ala Lys
        355                 360                 365

Ser Glu Ile Phe Asn Gly Asp Val Glu Trp Lys Ser Cys Asp Leu Glu
370                 375                 380

Glu Val Met Thr Asp Ala Leu Val Ser Asn Lys Pro Asp Phe Val Arg
385                 390                 395                 400
```

```
Leu Phe Val Asp Ser Gly Ala Asp Met Ala Glu Phe Leu Thr Tyr Gly
            405                 410                 415
Arg Leu Gln Gln Leu Tyr His Ser Val Ser Pro Lys Ser Leu Leu Phe
        420                 425                 430
Glu Leu Leu Gln Arg Lys His Glu Glu Gly Arg Leu Thr Leu Ala Gly
        435                 440                 445
Leu Gly Ala Gln Gln Ala Arg Glu Leu Pro Xaa Gly Leu Pro Ala Phe
    450                 455                 460
Ser Leu His Glu Val Ser Arg Val Leu Lys Asp Phe Leu His Asp Ala
465                 470                 475                 480
Cys Arg Gly Phe Tyr Gln Asp Gly Arg Xaa Xaa Xaa Xaa Arg Met Glu
                485                 490                 495
Glu Arg Gly Pro Pro Lys Arg Pro Ala Gly Gln Lys Trp Leu Pro Asp
                500                 505                 510
Leu Ser Arg Lys Ser Glu Asp Pro Trp Arg Asp Leu Phe Leu Trp Ala
        515                 520                 525
Val Leu Gln Asn Arg Tyr Glu Met Ala Thr Tyr Phe Trp Ala Met Gly
    530                 535                 540
Arg Glu Gly Val Ala Ala Ala Leu Ala Ala Cys Lys Ile Ile Lys Glu
545                 550                 555                 560
Met Ser His Leu Glu Lys Glu Ala Glu Val Ala Arg Thr Met Arg Glu
                565                 570                 575
Ala Lys Tyr Glu Gln Leu Ala Leu Asp Leu Phe Ser Glu Cys Tyr Ser
                580                 585                 590
Asn Ser Glu Asp Arg Ala Phe Ala Leu Leu Val Arg Arg Asn His Ser
                595                 600                 605
Trp Ser Arg Thr Thr Cys Leu His Leu Ala Thr Glu Ala Asp Ala Lys
        610                 615                 620
Ala Phe Phe Ala His Asp Gly Val Gln Ala Phe Leu Thr Lys Ile Trp
625                 630                 635                 640
Trp Gly Asp Met Ala Thr Gly Thr Pro Ile Leu Arg Leu Leu Gly Ala
                645                 650                 655
Phe Thr Cys Pro Ala Leu Ile Tyr Thr Asn Leu Ile Ser Phe Ser Glu
                660                 665                 670
Asp Ala Pro Gln Arg Met Asp Leu Glu Asp Leu Gln Glu Pro Asp Ser
                675                 680                 685
Leu Asp Met Glu Lys Ser Phe Leu Cys Ser Xaa Gly Gly Gln Leu Glu
    690                 695                 700
Lys Leu Thr Glu Ala Pro Arg Ala Pro Gly Asp Leu Gly Pro Gln Ala
705                 710                 715                 720
Ala Phe Leu Leu Thr Arg Trp Arg Lys Phe Trp Gly Ala Pro Val Thr
                725                 730                 735
Val Phe Leu Gly Asn Val Val Met Tyr Phe Ala Phe Leu Phe Leu Phe
                740                 745                 750
Thr Tyr Val Leu Leu Val Asp Phe Arg Pro Pro Gln Gly Pro Ser
        755                 760                 765
Gly Ser Glu Val Thr Leu Tyr Phe Trp Val Phe Thr Leu Val Leu Glu
    770                 775                 780
Glu Ile Arg Gln Gly Phe Phe Thr Asp Glu Asp Thr His Leu Val Lys
785                 790                 795                 800
Lys Phe Thr Leu Tyr Val Glu Asp Asn Trp Asn Lys Cys Asp Met Val
                805                 810                 815
```

```
Ala Ile Phe Leu Phe Ile Val Gly Val Thr Cys Arg Met Val Pro Ser
            820                 825                 830
Val Phe Glu Ala Gly Arg Thr Val Leu Ala Ile Asp Phe Met Val Phe
        835                 840                 845
Thr Leu Arg Leu Ile His Ile Phe Ala Ile His Lys Gln Leu Gly Pro
    850                 855                 860
Lys Ile Ile Ile Val Glu Arg Met Met Lys Asp Val Phe Phe Phe Leu
865                 870                 875                 880
Phe Phe Leu Ser Val Trp Leu Val Ala Tyr Gly Val Thr Thr Gln Ala
            885                 890                 895
Leu Leu His Pro His Asp Gly Arg Leu Glu Trp Ile Phe Arg Arg Val
        900                 905                 910
Leu Tyr Arg Pro Tyr Leu Gln Ile Phe Gly Gln Ile Pro Leu Asp Glu
    915                 920                 925
Ile Asp Glu Ala Arg Val Asn Cys Ser Leu His Pro Leu Leu Leu Glu
930                 935                 940
Ser Ser Ala Ser Cys Pro Asn Leu Tyr Ala Asn Trp Leu Val Ile Leu
945                 950                 955                 960
Leu Leu Val Thr Phe Leu Leu Val Thr Asn Val Leu Leu Met Asn Leu
            965                 970                 975
Leu Ile Ala Met Phe Ser Tyr Thr Phe Gln Val Val Gln Gly Asn Ala
        980                 985                 990
Asp Met Phe Trp Lys Phe Gln Arg Tyr His Leu Ile Val Glu Tyr His
        995                 1000                1005
Gly Arg Pro Ala Leu Ala Pro Pro Phe Ile Leu Leu Ser His Leu Ser
    1010                1015                1020
Leu Val Leu Lys Gln Val Phe Arg Lys Glu Ala Gln His Lys Arg Gln
1025                1030                1035                1040
His Leu Glu Arg Asp Leu Pro Asp Pro Leu Asp Gln Lys Ile Ile Thr
            1045                1050                1055
Trp Glu Thr Val Gln Lys Glu Asn Phe Leu Ser Thr Met Glu Lys Arg
        1060                1065                1070
Arg Arg Asp Ser Glu Gly Glu Val Leu Arg Lys Thr Ala His Arg Val
    1075                1080                1085
Asp Leu Ile Ala Lys Tyr Ile Gly Gly Leu Arg Glu Gln Glu Lys Arg
    1090                1095                1100
Ile Lys Cys Leu Glu Ser Gln Ala Asn Tyr Cys Met Leu Leu Leu Ser
1105                1110                1115                1120
Ser Met Thr Asp Thr Leu Ala Pro Gly Gly Thr Tyr Ser Ser Ser Gln
            1125                1130                1135
Asn Cys Gly Xaa Arg Ser Gln Pro Ala Ser Ala Arg Asp Arg Xaa Xaa
        1140                1145                1150
Xaa Xaa Xaa Xaa Glu Tyr Leu Glu Ala Gly Leu Pro Pro Ser Asp Thr
    1155                1160                1165
```

<210> SEQ ID NO 9
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

```
<400> SEQUENCE: 9

Gly Gly Gly Gly Gly Gly Gly Gly Gly Gly Gly Gly Gly Gly Gly
 1               5                  10                  15
Gly Gly Gly Gly Gly Gly Gly Gly Gly Gly Gly Gly Gly Gly Gly
                20                  25                  30
Gly Gly Gly Gly Gly Gly Gly Gly Gly Gly Gly Gly Gly Gly Gly
            35                  40                  45
Gly Gly Gly Gly Gly Gly Gly Gly Gly Gly Gly Gly Gly Gly Gly
        50                  55                  60
Gly Gly Gly Gly Gly Gly Gly Gly Gly Gly Gly Gly Gly Gly Gly
 65                 70                  75                  80
Gly Gly Gly Gly Gly Gly Gly Gly Gly Gly Gly Gly Gly Gly Gly
                85                  90                  95
Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly
            180                 185                 190
Gly Gly Gly Gly Gly Gly Gly Gly
        195                 200
```

METHODS AND COMPOSITIONS FOR TREATING AND DIAGNOSING DIABETES AND RELATED DISEASES INVOLVING BETA-TRP

CROSS-REFERENCE TO RELATED PATENT APPLICATIONS

The present application claims benefit of priority to U.S. Provisional Patent Application No. 60/452,596, filed Mar. 5, 2003, which is incorporated by reference in its entirety for any purpose.

BACKGROUND OF THE INVENTION

Diabetes mellitus can be divided into two clinical syndromes, Type 1 and Type 2 diabetes mellitus. Type 1, or insulin-dependent diabetes mellitus (IDDM), is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the level required for euglycemia (normal blood glucose level). Although the exact trigger for this immune response is not known, patients with IDDM have high levels of antibodies against pancreatic beta cells. However, not all patients with high levels of these antibodies develop IDDM.

Type 2 diabetes (also referred to as non-insulin dependent diabetes mellitus (NIDDM)) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type 2 diabetes.

Type 2 diabetes is brought on by a combination of poorly understood genetic and acquired risk factors—including a high-fat diet, lack of exercise, and aging. Worldwide, Type 2 diabetes has become an epidemic, driven by increases in obesity and a sedentary lifestyle, widespread adoption of western dietary habits, and the general aging of the populations in many countries. In 1985, an estimated 30 million people worldwide had diabetes—by 2000, this figure had increased 5-fold, to an estimated 154 million people. The number of people with diabetes is expected to double between now and 2025, to about 300 million.

Type 2 diabetes is a complex disease characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. As discussed above, one of the principal underlying causes of diabetes is the inability of beta cells to produce sufficient insulin to maintain glucose levels. Therefore, an important therapeutic goal in the treatment of diabetes is therefore to increase insulin production. The present invention addresses this and other problems.

BRIEF SUMMARY OF THE INVENTION

The present invention provides methods of identifying an agent that induces glucose-stimulated insulin production in an animal. In some embodiments, the method comprising the steps of: (i) contacting an agent to a polypeptide comprising at least 20 contiguous amino acids of SEQ ID NO:2; (ii)selecting an agent that binds to the polypeptide or enhances the expression or activity of the polypeptide, and (iii) determining the effect of the selected agent on glucose-stimulated insulin secretion, thereby identifying an agent that induces glucose-stimulated insulin production in an animal.

In some embodiments, step (ii) comprises selecting an agent that enhances the expression of the polypeptide. In some embodiments, step (ii) comprises selecting an agent that enhances the activity of the polypeptide. In some embodiments, step (ii) comprises selecting an agent that binds to the polypeptide.

In some embodiments, the polypeptide comprises SEQ ID NO:2.

In some embodiments, the polypeptide is expressed in a cell and the contacting step comprises contacting the agent to the cell. In some embodiments, an agent is selected that enhances polypeptide activity and the activity of the polypeptide is determined by a step comprising measuring a change in calcium flux in the cell. In some embodiments, an agent is selected that enhances polypeptide activity and the activity of the polypeptide is determined by a step comprising measuring a change in membrane potential of the cell.

In some embodiments, the membrane potential of the cell is measured be detecting a change in fluorescence of a dye whose fluorescence is dependent on cell depolarization and wherein the change in fluorescence is detected with a device sufficient for high throughput screening. In some embodiments, the cell is an insulin-secreting cell. In some embodiments, the cell is a pancreatic β cell.

In some embodiments, the polypeptide is recombinantly expressed in the cell. In some embodiments, the cell is a Chinese hamster ovary (CHO) cell.

In some embodiments, the method further comprising administering the agent to a diabetic animal and testing the animal for increased glucose-stimulated insulin secretion. In some embodiments, the animal is selected from a ZDF rat and a db/db mouse.

In some embodiments, the polypeptide comprises at least 100 amino acids. In some embodiments, the polypeptide is at least 80% identical to SEQ ID NO:2.

The present invention also provides methods of inducing glucose-stimulated insulin production in an animal. In some embodiments, the methods comprise administering a therapeutically effective amount of the agent selected in a method comprising the steps of: (i) contacting an agent to a polypeptide comprising at least 20 contiguous amino acids of SEQ ID NO:2; (ii)selecting an agent that binds to the polypeptide or enhances the expression or activity of the polypeptide, and (iii) determining the effect of the selected agent on glucose-stimulated insulin secretion. In some embodiments, the animal is a human. In some embodiments, the human has Type 2 diabetes. In some embodiments, the human is predisposed for Type 2 diabetes.

The present invention also provides methods of expressing βTRP in a pancreatic islet cell. In some embodiments, the method comprises introducing into an islet cell a polynucleotide encoding a polypeptide comprising at least 20 contiguous amino acids of SEQ ID NO:2. In some embodiments, the islet cell is defective for glucose-stimulated insulin secretion.

In some embodiments, the polynucleotide is introduced in vitro. In some embodiments, the polynucleotide is introduced in vivo.

In some embodiments, the polypeptide comprises at least 100 amino acids. In some embodiments, the polypeptide is at least 80% identical to SEQ ID NO:2. In some embodiments, the polypeptide comprises SEQ ID NO:2. In some embodiments, the polynucleotide comprises SEQ ID NO:1.

In some embodiments, the islet cell is a β cell.

DEFINITIONS

A person is "predisposed for diabetes" when the person is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m$^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" *Diabetes Care* 25(1): S5–S24 (2002).

A "βTRP" or "beta-TRP" polypeptide refers to a calcium channel that is substantially identical to SEQ ID NO:2, SEQ ID NO:4, or SEQ ID NO:6. βTRP polypeptides, when inserted into a membrane or expressed in a cell, typically form a functional cation channel. In some embodiments, amino acid residues conserved between mouse and human (see, FIGS. 7A–7D), rat and human, rat and mouse or between all three sequences are present in βTRP sequences of the invention. In some cases, βTRP comprises a glutamine (e.g., encoded by the codon CAG) or an arginine (e.g., encoded by the codon CGG) at position 579. βTRP polypeptides typically have a "TRP" motif and transmembrane domains. See, e.g., FIG. 8 illustrating these motifs and domains in the human βTRP sequence.

"βTRP activity," as used herein, refers to the ability of a protein to set or modulate electrical potential of the plasma membrane of a cell. One can use fluorescent dyes or fluorescent resonance energy transfer (FRET) reagents that are sensitive to membrane potential to detect the activity of a channel in a cell. See, e.g., Miller et al., *Eur J Pharmacol.* 370(2):179–85 (1999); Fedida, et al., *Prog Biophys Mol Biol* 75(3):165–99 (2000). Alternatively, calcium flux assays using calcium-dependent fluorescent dyes can be used to detect channel activity. Activity can also be measured, for example, using patch-clamp techniques. Patch-clamp analysis generally involves formation of a high resistance seal between the cell membrane and the glass wall of a micropipette. Current passing through the ion channels in the membrane is then measured.

An "activator of βTRP" refers to an agent that opens, stimulates, sensitizes or up regulates the activity or expression of βTRP. "Enhanced βTRP activity" refers to activity of a βTRP channel that is opened, stimulated, sensitized or up-regulated compared to a control (e.g., a sample not containing a potential βTRP modulator).

"A dye whose fluorescence is dependent on cell depolarization" refers to dyes or probes that exhibit potential-dependent changes in their transmembrane distribution that are accompanied by a fluorescence change. The magnitude of their optical responses can be about 1% fluorescence change per mV. These dyes, sometimes referred to as "slow-response probes," include, e.g., cationic carbocyanines and rhodamines and anionic oxonols, as well as proprietary dyes available for the Molecular Devices (Sunnyvale, Calif.) FLEXstation and FLIPR systems. Dyes that fluoresce in response to changes in membrane potential and cell depolarization are described in, e.g., Zochowski M, et al. *Biol Bull* 198, 1–21 (2000); Shapiro, H M, *Methods* 21, 271–279 (2000); Nicholls D G, et al. *Trends Neurosci* 23, 166–174 (2000); Loew L M. *Cell Biology: A Laboratory Handbook,* 2nd Ed., Vol. 3, Celis J E, Ed. pp. 375–379 (1998); Plasek J, et al. *J Photochem Photobiol* B 33, 101–124 (1996); Loew L M. *Pure Appl Chem* 68, 1405 (1996); Loew L M. *Adv Chem Ser* 235, 151 (1994); and Smith J C. *Biochim Biophys Acta* 1016, 1–28 (1990).

Increases or decreases in membrane potential are also referred to as "membrane hyperpolarization" and "membrane depolarization," respectively.

"A device sufficient for high throughput screening" refers to a device that can be used by one person to analyze a large number of samples (e.g., at least 96 and sometimes at least 200, 384, 500 or even 1000 samples on a daily basis). Examples of high throughput devices for use in measuring cell depolarization and membrane potential changes include, e.g., the FLIPR and FLEXstation devices from Molecular Devices (Sunnyvale, Calif.). Methods such as patch-clamping are not practical for high throughput analyses.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology,* Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al. (1992); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. The term "substantially identical" refers to two or more sequences that have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. The present invention provides polynucleotides and polypeptides substantially identical to SEQ ID NOs:1, 2, 3, 4, 5, and 6.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length. The present invention provides polypeptides substantially similar to SEQ ID NOs: 2, 4, and 6.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389–3402, and Altschul et al. (1990) *J. Mol. Biol.* 215:403–410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30C for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual,* Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors," "activators," and "modulators" of βTRP expression or of βTRP activity are used to refer to inhibitory, activating, or modulating molecules, respectively, identified using in vitro and in vivo assays for βTRP expression or βTRP activity, e.g., ligands, agonists, antagonists, and their homologs and mimetics. The term "modulator" includes inhibitors and activators. Inhibitors are agents that, e.g., inhibit expression of βTRP or bind to, partially or totally block stimulation or enzymatic activity, decrease, prevent, delay activation, inactivate, desensitize, or down regulate the activity of βTRP, e.g., antagonists. Activators are agents that, e.g., induce or activate the expression of βTRP or bind to, stimulate, increase, open, activate, facilitate, enhance activation or enzymatic activity, sensitize or up regulate the activity of βTRP, e.g., agonists. Modulators include naturally occurring and synthetic ligands, antagonists, agonists, small chemical molecules and the like. Such assays for inhibitors and activators include, e.g., applying putative modulator compounds to pancreatic cells or other cells expressing βTRP, in the presence or absence of βTRP modulators and then determining the functional effects on βTRP activity, as described above. Samples or assays comprising βTRP that are treated with a potential activator, inhibitor, or modulator are compared to control samples without the inhibitor, activator, or modulator to examine the extent of effect. Control samples (untreated with modulators) are assigned a relative βTRP activity value of 100%. Inhibition of βTRP is achieved when the βTRP activity value relative to the control is about 80%, optionally 50% or 25–1%. Activation of βTRP is achieved when the βTRP activity value relative to the control is 110%, optionally 150%, optionally 200–500%, or 1000–3000% higher.

BRIEF DESCRIPTION OF THE DRAWINGS

FIG. 1A displays a custom mouse islet oligonucleotide array analysis of probe set MBXMUSISL08907. Average difference values reflect the relative abundance of βTRP in mouse islets and the insulin secreting mouse cell line betaHC9. FIG. 1B displays how the rat islet custom oligonucleotide array was used to survey gene changes in animal models of diabetes. βTRP mRNA (probe set MBXRATISL12881) is decreased 2–3 fold (p=0.002) in ZDF female rats relative to lean control animals and is substantially restored by concomitant treatment with troglitazone.

FIGS. 7A–D provide an alignment of the human (SEQ ID NO:7), rat (SEQ ID NO:6) and mouse (SEQ ID NO:4) βTRP amino acid sequences.

FIG. 8 depicts the βTRP amino acid sequence (SEQ ID NO:2). Transmembrane domains are underlined. The TRP motif is in bold.

DETAILED DESCRIPTION OF THE INVENTION

I. Introduction

Figure 1:
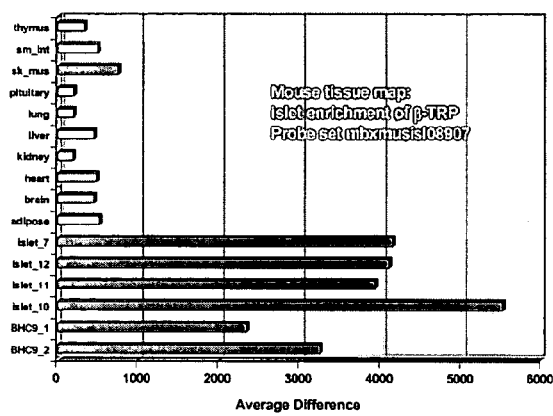
FIG. 1 displays array expression data for βTRP.
Figure 1:
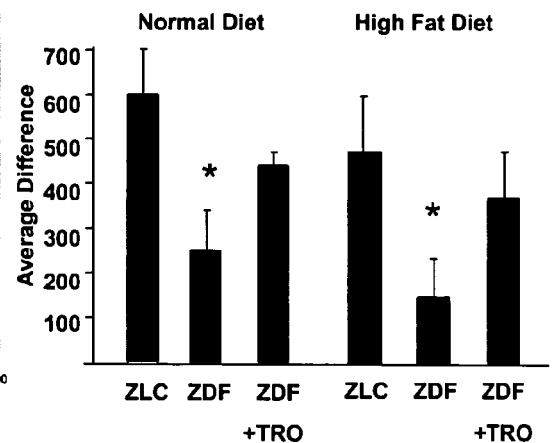

The present application demonstrates that, surprisingly, βTRP expression in pancreatic islet cells effects insulin secretion. Expression of βTRP is relatively islet cell specific. In ZDF rats (an animal model for diabetes), βTRP expression is reduced compared to wild type rats. Significantly, when βTRP is expressed in ZDF islet cells, glucose stimulated insulin secretion is increased compared to empty vector controls. These results demonstrate that enhancing expression or activity of βTRP in insulin secreting cells increases glucose-stimulated insulin production. Therefore, the present application provides methods for identifying agents that increase βTRP expression or activity in insulin secreting cells, as well as the use of such agents to treat diabetic or pre-diabetic individuals. The application also provides methods for introducing βTRP-encoding polynucleotides into pancreatic β cells for the expression of βTRP.

II. General Recombinant Nucleic Acid Methods for Use with the Invention

The nucleic acid compositions used in the subject invention may encode all or a part, usually at least substantially all, of the βTRP polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nucleotides, more usually at least about 18 nucleotides to about 20 nucleotides, more usually at least about 25 nucleotides to about 50 nucleotides. Such small DNA fragments are useful as primers for PCR, hybridization screening, siRNA, etc. Larger DNA fragments, i.e. greater than 100 nucleotides are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art or as described herein. In some embodiments, a pair of primers is chosen that will generate an amplification product of at least about 50 nucleotides or at least about 100 nucleotides. Algorithms for the selection of primer sequences are generally known, and are available in commercial software packages. Amplification primers hybridize to complementary strands of DNA, and will prime towards each other.

The βTRP-encoding nucleic acids are isolated and obtained in substantial purity, generally as other than an intact mammalian chromosome. Usually, the DNA will be obtained substantially free of other nucleic acid sequences can be typically "recombinant", i.e. flanked by one or more nucleotides with which it is not normally associated on a naturally occurring chromosome.

The sequence of βTRP polypeptides (or polynucleotide coding regions or flanking promoter regions) can be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and can differ by at least two, or by at least about ten or more nucleotides or amino acids. In general, the sequence changes can be substitutions, insertions or deletions. Deletions can further include larger changes, such as deletions of a domain or exon. It should be noted that TRP channel sequences are conserved mainly within the transmembrane domain, and regions outside this domain therefore are more likely targets for mutagenesis without affecting function. For example, FIG. 7 illustrates the alignment of rat, mouse and human sequences. In some embodiments, the βTRP nucleic acids of the invention encode polypeptides, or fragments thereof, comprising the amino acids conserved between mouse and human sequences. In other embodiments, the βTRP nucleic acids encode polypeptides, or fragments thereof, comprising amino acids conserved between human and rat or between rat, mouse and human sequences.

Techniques for in vitro mutagenesis of cloned genes are known. Examples of protocols for scanning mutations may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual* (CSH Press, 1989), pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989).

In numerous embodiments of the present invention, nucleic acids encoding a βTRP of interest will be isolated and cloned using recombinant methods. Such embodiments are used, e.g., to isolate βTRP polynucleotides (e.g., SEQ ID NO:1, SEQ ID NO:3, or SEQ ID NO:5) for protein expression or during the generation of variants, derivatives, expression cassettes, or other sequences encoding a βTRP polypeptide (e.g., SEQ ID NO:2, SEQ ID NO:4, or SEQ ID NO:6), to monitor βTRP gene expression, for the isolation or detection of βTRP sequences in different species, for diagnostic purposes in a patient, e.g., to detect mutations in βTRP or to detect expression levels of βTRP nucleic acids or βTRP polypeptides. In some embodiments, the sequences encoding the βTRP of the invention are operably linked to a heterologous promoter. In one embodiment, the nucleic acids of the invention are from any mammal, including, in particular, e.g., a human, a mouse, a rat, etc.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences (e.g., SEQ ID NO:1) encoding βTRP that provide a reference for PCR primers and defines suitable regions for isolating βTRP-specific probes. Alternatively, where the sequence is cloned into an expression library, the expressed recombinant protein can be detected immunologically with antisera or purified antibodies made against the βTRP of interest.

Methods for making and screening genomic and cDNA libraries are well known to those of skill in the art (see, e.g., Gubler and Hoffman *Gene* 25:263–269 (1983); Benton and Davis *Science,* 196:180–182 (1977); and Sambrook, supra). Pancreatic cells are an example of suitable cells to isolate βTRP RNA and cDNA.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5–100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961–3965 (1975).

An alternative method combines the use of synthetic oligonucleotide primers with polymerase extension on an mRNA or DNA template. Suitable primers can be designed from specific βTRP sequences, e.g., the sequences set forth in SEQ ID NO:1. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a βTRP polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying the genes encoding a βTRP polypeptide of the invention from mammalian tissues can be derived from the sequences provided herein, such as SEQ ID NO:1, or encoding amino acid sequences within βTRP polypeptides, e.g., SEQ ID NO:2. For a general overview of PCR, see, Inis et al. *PCR Protocols: A Guide to Methods and Applications, Academic Press,* San Diego (1990).

Synthetic oligonucleotides can be used to construct genes. This is done using a series of overlapping oligonucleotides, usually 40–120 bp in length, representing both the sense and anti-sense strands of the gene. These DNA fragments are then annealed, ligated and cloned.

A gene encoding a βTRP polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Introduction of Polynucleosides Encoding βTRP Into Cells

Where the βTRP nucleic acid to be delivered into a cell is DNA, any construct having a promoter (e.g., a promoter that is functional in a eukaryotic cell) operably linked to a βTRP DNA of interest, or allowing for linkage to an endogenous promoter upon introduction into a genome, can be used in the invention. The constructs containing the βTRP DNA sequence (or the corresponding RNA sequence) can be any eukaryotic expression construct containing the βTRP DNA or the RNA sequence of interest. For example, a plasmid or viral construct (e.g. adenovirus) can be cleaved to provide linear DNA having ligatable termini. These termini are bound to exogenous DNA having complementary-like ligatable termini to provide a biologically functional recombinant DNA molecule having an intact replicon and a desired phenotypic property. Preferably the construct is capable of replication in eukaryotic and/or prokaryotic hosts (viruses in eukaryotic, plasmids in prokaryotic), which constructs are known in the art and are commercially available.

The constructs can be prepared using techniques well known in the art. Likewise, techniques for obtaining expression of exogenous DNA or RNA sequences in a genetically altered host cell are known in the art (see, for example, Kormal et al., *Proc. Natl. Acad. Sci. USA*, 84:2150–2154 (1987); Sambrook et al. *Molecular Cloning: a Laboratory Manual*, 2nd Ed., 1989, Cold Spring Harbor Laboratory Press, Cold Spring Harbor, N.Y).

In some embodiments, the DNA construct contains a promoter to facilitate expression of the DNA of interest within a pancreatic (e.g., an islet) cell. The promoter can be a strong, viral promoter that functions in eukaryotic cells such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521–530 (1985)) and the promoter from the long terminal repeat (LTR) of RSV (Gorman et al., *Proc. Natl. Acad. Sci. USA* 79:6777–6781 (1982)).

Alternatively, the promoter used can be a strong general eukaryotic promoter such as the actin gene promoter. In one embodiment, the promoter used can be a tissue-specific promoter. For example, the promoter used in the construct can be a pancreas-specific promoter, a duct cell specific promoter or a stem cell-specific promoter. Exemplary β cell-specific promoters include the insulin and amylin promoters. The constructs of the invention can also include sequences (e.g., enhancers) in addition to promoters which enhance expression in the target cells In another embodiment, the promoter is a regulated promoter, such as a tetracycline-regulated promoter, expression from which can be regulated by exposure to an exogenous substance (e.g., tetracycline.).

Other components such as a marker (e.g., an antibiotic resistance gene (such as an ampicillin resistance gene) or β-galactosidase) aid in selection or identification of cells containing and/or expressing the construct, an origin of replication for stable replication of the construct in a bacterial cell (preferably, a high copy number origin of replication), or other elements which facilitate production of the DNA construct, the protein encoded thereby, or both.

For eukaryotic expression, the construct should contain at a minimum a eukaryotic promoter operably linked to a DNA of interest, which is in turn operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. The construct may also include one or more introns, where appropriate, which can increase levels of expression of the DNA of interest, particularly where the DNA of interest is a cDNA (e.g., contains no introns of the naturally-occurring sequence). Any of a variety of introns known in the art may be used.

In an alternative embodiment, the nucleic acid delivered to the cell is an RNA encoding βTRP. In this embodiment, the RNA is adapted for expression (i.e., translation of the RNA) in a target cell. Methods for production of RNA (e.g., mRNA) encoding a protein of interest are well known in the art, and can be readily applied to the product of RNA encoding βTRP useful in the present invention.

A. Delivery of βTRP-Encoding Nucleic Acid

Delivery of βTRP-encoding nucleic acids can be accomplished using any means known in the art. For example, delivery can be accomplished using a viral or a non-viral vector. In some embodiments, the nucleic acid is delivered within a viral particle, such as an adenovirus. In another embodiment, the nucleic acid is delivered in a formulation comprising naked DNA admixed with an adjuvant such as viral particles (e.g., adenovirus) or cationic lipids or liposomes. An "adjuvant" is a substance that does not by itself produce the desired effect, but acts to enhance or otherwise improve the action of the active compound. The precise vector and vector formulation used will depend upon several factors, such as the size of the DNA to be transferred, the delivery protocol to be used, and the like. Exemplary non-viral and viral vectors are described in more detail below.

1. Viral Vectors

In general, viral vectors used in accordance with the invention are composed of a viral particle derived from a naturally-occurring virus which has been genetically altered to render the virus replication-defective and to deliver a recombinant gene of interest for expression in a target cell in accordance with the invention. Numerous viral vectors are well known in the art, including, for example, retrovirus, adenovirus, adeno-associated virus, herpes simplex virus (HSV), cytomegalovirus (CMV), vaccinia and poliovirus vectors. The viral vector can be selected according to its preferential infection of the cells targeted Where a replication-deficient virus is used as the viral vector, the production of infectious virus particles containing either DNA or RNA corresponding to the DNA of interest can be achieved by introducing the viral construct into a recombinant cell line which provides the missing components essential for viral replication. In one embodiment, transformation of the recombinant cell line with the recombinant viral vector will not result in production or substantial production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., *Science* 252:431–434 (1991) and Rosenfeld et al., *Cell* 68:143–155 (1992) (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., *J. Virol.* 67:2928–2931 (1993); Takeuchi et al., *Archiv. Virol.*, 128:177–183 (1993); Tanabayashi et al., *Virol.* 187:801–804 (1992); Kawano et al., *Virol.,* 179:857–861 (1990); Elango et al., *J. Gen. Virol.* 69:2893–28900 (1988).

2. Non-Viral Vectors

The nucleic acids of interest can be introduced into a cell using a non-viral vector. "Non-viral vector" as used herein is meant to include naked DNA (e.g., DNA not contained within a viral particle, and free of a carrier molecules such as lipids), chemical formulations comprising naked nucleic acid (e.g., a formulation of DNA (and/or RNA) and cationic compounds (e.g., dextran sulfate, cationic lipids)), and naked nucleic acid mixed with an adjuvant such as a viral particle (e.g., the DNA of interest is not contained within the viral particle, but the formulation is composed of both naked DNA and viral particles (e.g., adenovirus particles) (see, e.g., Curiel et al., *Am. J. Respir. Cell Mol. Biol.* 6:247–52 (1992)).

In some embodiments, the formulation comprises viral particles which are mixed with the naked DNA construct prior to administration. In some embodiments, the viral particles are adenovirus particles. See, e.g., Curiel et al., *Am. J. Respir. Cell Mol. Biol.* 6:247–52 (1992)).

Alternatively or in addition, the nucleic acid can be complexed with polycationic substances such as poly-L-lysine or DEAC-dextran, targeting ligands, and/or DNA binding proteins (e.g., histones). DNA- or RNA-liposome complex formulations comprise a mixture of lipids which bind to genetic material (DNA or RNA) and facilitate delivery of the nucleic acid into the cell. Liposomes which can be used in accordance with the invention include DOPE (dioleyl phosphatidyl ethanol amine), CUDMEDA (N-(5-cholestrum-3-.beta.-ol 3-urethanyl)-N',N'-dimethylethylene diamine).

For example, the naked DNA can be administered in a solution containing Lipofectin™ (LTI/BRL) at concentrations ranging from about 2.5% to 15% volume:volume, e.g., about 6% to 12% volume:volume. Exemplary methods and compositions for formulation of DNA for delivery according to the method of the invention are described in U.S. Pat. No. 5,527,928.

The nucleic acid of interest can also be administered as a chemical formulation of DNA or RNA coupled to a carrier molecule (e.g., an antibody or a receptor ligand) which facilitates delivery to host cells. By the term "chemical formulations" is meant modifications of nucleic acids which allow coupling of the nucleic acid compounds to a carrier molecule such as a protein or lipid, or derivative thereof. Exemplary protein carrier molecules include antibodies specific to the cells of a targeted pancreatic cell or receptor ligands, e.g., molecules capable of interacting with receptors associated with a cell of a targeted pancreatic cell.

B. Introduction of βTRP Nucleic Acids into Pancreatic Cells In Vitro

Nucleic acids encoding βTRP can be introduced into a cell in vitro to accomplish expression in the cell to provide for at least transient expression. The cells into which the nucleic acid is introduced can be differentiated epithelial cells (e.g., pancreatic cells (including, e.g., islet cells such as β-cells), gut cells, hepatic cells or duct cells), pluripotent adult or embryonic stem cells, or any mammalian cell capable of developing into β cells or cells capable of expression of insulin in vitro. The cell can be subsequently implanted into a subject having a disorder characterized by a deficiency in insulin (e.g., type 1 or 2 diabetes), which disorder is amenable to treatment by islet cell replacement therapy. In some embodiments, the host cell in which βTRP expression is provided and which is implanted in the subject is derived from the individual who will receive the transplant (e.g., to provide an autologous transplant). Alternatively, cells from another subject (the "donor") could be modified to express βTRP, and the cells subsequently implanted in the affected subject to provide for insulin production.

Introduction of nucleic acid into the cell in vitro can be accomplished according to methods well known in the art (e.g., through use of electroporation, microinjection, lipofection infection with a recombinant (preferably replication-deficient) virus, and other means well known in the art). The nucleic acid is generally operably linked to a promoter that facilitates a desired level of polypeptide expression (e.g., a promoter derived from CMV, SV40, adenovirus, or a tissue-specific or cell type-specific promoter). Transformed cells containing the recombinant nucleic acid can be selected and/or enriched via, for example, expression of a selectable marker gene present in the introduced construct or that is present on a nucleic acid that is co-transfected with the construct. Typically selectable markers provide for resistance to antibiotics such as tetracycline, hygromycin, neomycin, and the like. Other markers can include thymidine kinase and the like. Other markers can include markers that can be used to identify βTRP-expressing cells, such as β-galactosidase or green florescent protein.

Expression of the introduced nucleic acid in the transformed cell can be assessed by various methods known in the art. For example, expression of the introduced gene can be examined by northern blot to detect mRNA which hybridizes with a DNA probe derived from the relevant gene. Those cells that express the desired gene can be further isolated and expanded in in vitro culture using methods well known in the art. The host cells selected for transformation will vary with the purpose of ex vivo therapy (e.g., insulin production), the site of implantation of the cells, and other factors that will vary with a variety of factors that will be appreciated by the ordinarily skilled artisan.

The transformed cell can also be examined for insulin production. For example, expression of insulin could be detected by PCR, northern blot, immunocytochemistry, western blot or ELISA. Alternatively a marker gene such as green florescent protein or an antibiotic resistance gene operatively linked to an islet specific promoter such as the insulin gene promoter could be used for identification or selection of transformed islet cells.

Methods for engineering a host cell for expression of a desired gene product(s) and implantation or transplantation of the engineered cells (e.g., ex vivo therapy) are known in the art (see, e.g., Gilbert et al., *Transplantation* 56:423–427 (1993)). For expression of a desired gene in exogenous or autologous cells and implantation of the cells (e.g., islet cells) into pancreas, see, e.g., Docherty, *Clin Sci (Colch)* 92:321–330 (1997); Hegre et al. *Acta Endocrinol Suppl (Copenh)* 205:257–281 (1976); Sandler et al., *Transplantation* 63:1712–1718 (1997); Calafiore, *Diabetes Care* 20:889–896 (1997); Kenyon et al., *Diabetes Metab Rev* 12:361–372 (1996); Chick et al., *Science* 197:780–782 (1977). In general, the cells can be implanted into the pancreas, or to any practical or convenient site, e.g., subcutaneous site, liver, peritoneum.

Methods for transplanting islets cells are well known in the art, see, e.g., Hegre et al. *Acta Endocrinol Suppl (Copenh)* 205:257–281 (1976); Sandler et al. *Transplantation* 63:1712–1718 (1997); Calafiore, *Diabetes Care* 20:889–896 (1997); Kenyon et al., *Diabetes Metab Rev* 12:361–372 (1996); Chick et al., *Science* 197:780–782 (1977).

In general, after expansion of the transformed cells in vitro, the cells can be implanted into the mammalian subject by methods well known in the art. The number of cells implanted is a number of cells sufficient to provide for expression of levels of insulin sufficient to lower blood glucose levels. The number of cells to be transplanted can be determined based upon such factors as the levels of polypeptide expression achieved in vitro, and/or the number of cells that survive implantation. The transformed cells are implanted in an area of dense vascularization such as the liver, and in a manner that minimizes surgical intervention in the subject. The engraftment of the implant of transformed cells is monitored by examining the mammalian subject for classic signs of graft rejection, i.e., inflammation and/or exfoliation at the site of implantation, and fever, and by monitoring blood glucose levels.

C. Introduction of βTRP Nucleic Acids into Pancreatic Cells In Vivo

βTRP nucleic acids can be delivered directly to a subject to provide for βTRP expression in a target cell (e.g., a pancreatic islet cell), thereby promoting glucose-stimulated insulin production. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, or pneumatic injection using a gene gun).

In general, the transformed cells expressing the protein encoded by the DNA of interest produce a therapeutically effective amount of βTRP to produce islet cells, in particular β-cells in the mammalian patient capable of glucose-stimulated insulin production. In some embodiments, the introduced DNA also encodes an islet-specific transcription factor or other polypeptide that controls or stimulates insulin production in islet cells.

In general terms, the delivery method comprises introducing the nucleic of interest-containing vector into a pancreatic cell. By way of example, a βTRP DNA-containing vector may comprise either a viral or non-viral vector (including naked DNA), which is introduced into the pancreas in vivo via the duct system. Intraductal administration can be accomplished by cannulation by, for example, insertion of the cannula through a lumen of the gastrointestinal tract, by insertion of the cannula through an external orifice, or insertion of the cannula through the common bile duct. Retrograde ductal administration may be accomplished in the pancreas by endoscopic retrograde chalangio-pancreatography (ECRP). Exemplary methods for accomplishing intraductal delivery to the pancreas are described in U.S. Pat. No. 6,004,944.

The precise amount of βTRP-encoding nucleic acid administered will vary greatly according to a number of factors including the susceptibility of the target cells to transformation, the size and weight of the subject, the levels of protein expression desired, and the condition to be treated. The amount of nucleic acid and/or the number of infectious viral particles effective to infect the targeted tissue, transform a sufficient number of cells, and provide for production of a desired level of insulin can be readily determined based upon such factors as the efficiency of the transformation in vitro and the susceptibility of the targeted cells to transformation. For example, the amount of DNA introduced into the pancreatic duct of a human is, for example, generally from about 1 μg to about 750 mg, e.g., from about 500 μg to about 500 mg, e.g., from about 10 mg to about 200 mg, e.g., about 100 mg. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Pancreatic cells modified according to the invention can facilitate sufficiently high levels of expression of a nucleic acid of interest, e.g., where the nucleic acid delivered is DNA and the DNA of interest is operably linked to a strong eukaryotic promoter (e.g., CMV, MMTV). The expressed protein can induce glucose-stimulated insulin production in islet cells. Thus the methods of the invention are useful in treating a mammalian subject having a variety of insulin related conditions.

The actual number of transformed pancreatic cells required to achieve therapeutic levels of the protein of interest will vary according to several factors including the protein to be expressed, the level of expression of the protein by the transformed cells, the rate in which the protein induces insulin production, and the condition to be treated.

Regardless of whether the islet transcription factor-encoding nucleic acid is introduced in vivo or ex vivo, the nucleic acid (or islet cells produced in vitro or recombinant cells expressing the βTRP nucleic acid that are to be transplanted for development into islet cells in vivo post-transplantation) can be administered in combination with other genes and other agents.

D. Assessment of Therapy

The effects of ex vivo or in vivo therapy according to the methods of the invention can be monitored in a variety of ways. Generally, a sample of blood from the subject can be assayed for, for example, levels of glucose, proinsulin, c-peptide, and insulin. Appropriate assays for detecting proinsulin, c-peptide, insulin and glucose in blood samples are well known in the art.

IV. Identification of Modulators of βTRP

Modulators of βTRP, i.e. agonists or antagonists of βTRP activity or βTRP polypeptide or polynucleotide expression, are useful for treating a number of human diseases, including diabetes. Administration of βTRP activators can be used to treat diabetic (e.g., Type 2) individuals.

A. Agents that Modulate βTRP

The agents tested as modulators of βTRP can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Activators will include molecules that directly activate (open) βTRP as well as molecules that activate regulators (GPCRs, G-proteins, etc.) that subsequently activate βTRP. Modulators also include agents designed to reduce the level of βTRP mRNA (e.g. antisense molecules, ribozymes, DNAzymes, small inhibitory RNAs (siRNAs) and the like) or the level of translation from an mRNA (e.g., translation blockers such as an antisense molecules that are complementary to translation start or other sequences on an mRNA molecule). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Generally, the compounds to be tested are present in the range from 1 pM to 100 mM.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Methods of Screening for Modulators of βTRP

A number of different screening protocols can be utilized to identify agents that modulate the level of expression or activity of βTRP in cells, particularly mammalian cells, and especially human cells. In general terms, the screening methods involve screening a plurality of agents to identify an agent that modulates the activity of βTRP by, e.g., binding to a βTRP polypeptide, preventing an inhibitor or activator from binding to βTRP, increasing association of an inhibitor or activator with βTRP, or activating or inhibiting expression or activity of βTRP.

In some embodiments, different TRP polypeptides (e.g., TRPC1, TRPC1, TRPC2, TRPC3, TRPC4, TRPC5, TRPC6, TRPC7, TRPV1, TRPV2, TRPV3, TRPV4, TRPV5, TRPV6, TRPM1, TRPM2, TRPM3, TRPM4, TRPM5, TRPM6, TRPM7, and TRPM8) are screened in parallel to identify an agent that modulates βTRP but not at least one other TRP channel.

1. βTRP Binding Assays

Preliminary screens can be conducted by screening for agents capable of binding to βTRP, as at least some of the agents so identified are likely βTRP modulators. Binding assays are also useful, e.g., for identifying endogenous proteins that interact with βTRP. For example, antibodies, receptors or other molecules that bind βTRP can be identified in binding assays.

Binding assays usually involve contacting a βTRP protein with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61–89. Other binding assays involve the use of mass spectrometry or NMR techniques to identify molecules bound to βTRP or displacement of labeled substrates. The βTRP protein utilized in such assays can be naturally expressed, cloned or synthesized.

In addition, mammalian or yeast two-hybrid approaches (see, e.g., Bartel, P. L. et. al. Methods Enzymol, 254:241 (1995)) can be used to identify polypeptides or other molecules that interact or bind when expressed together in a cell.

2. Expression Assays

Screening for a compound that modulates the expression of βTRP are also provided. Screening methods generally involve conducting cell-based assays in which test compounds are contacted with one or more cells expressing βTRP, and then detecting an increase or decrease in βTRP expression (either transcript, translation product). Assays can be performed with cells that naturally express βTRP or in cells recombinantly altered to express βTRP.

βTRP expression can be detected in a number of different ways. As described infra, the expression level of βTRP in a cell can be determined by probing the mRNA expressed in a cell with a probe that specifically hybridizes with a transcript (or complementary nucleic acid derived therefrom) of βTRP. Probing can be conducted by lysing the cells and conducting northern blots or without lysing the cells using in situ-hybridization techniques. Alternatively, βTRP protein can be detected using immunological methods in which a cell lysate is probed with antibodies that specifically bind to βTRP.

Other cell-based assays involve reporter assays conducted with cells using standard reporter gene assays. These assays can be performed in either cells that do, or do not, express βTRP. Some of these assays are conducted with a heterologous nucleic acid construct that includes a βTRP promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) *Nature* 282:864–869), luciferase, β-galactosidase and alkaline phosphatase (Toh, et al. (1980) *Eur. J. Biochem.* 182:231–238; and Hall et al. (1983) *J. Mol. Appl. Gen.* 2:101).

In these assays, cells harboring the reporter construct are contacted with a test compound. Modulated promoter expression is monitored by detecting the level of a detectable reporter. A number of different kinds of βTRP modulators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of βTRP expression levels for a control population (e.g., lean individuals not having or at risk for Type 2 diabetes) or cells (e.g., tissue culture cells not exposed to a βTRP modulator). Expression levels can also be determined for cells that do not express βTRP as a negative control. Such cells generally are otherwise substantially genetically the same as the test cells.

A variety of different types of cells can be utilized in the reporter assays. Cells that express an endogenous βTRP include, e.g., pancreatic cells such as islet cells, e.g., β cells. Cells that do not endogenously express βTRP can be prokaryotic or eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HepG2, COS, CHO and HeLa cell lines. *Xenopus* oocytes can also be used.

Various controls can be conducted to ensure that an observed activity is authentic including running parallel reactions with cells that lack the reporter construct or by not contacting a cell harboring the reporter construct with test compound. Compounds can also be further validated as described below.

3. Activity

Analysis of βTRP polypeptide activity is performed according to general biochemical procedures. Such assays include cell-based assays as well as in vitro assays involving purified or partially purified βTRP polypeptides or crude cell lysates. In some embodiments, the βTRP polypeptide is expressed on a cell and the cell is contacted with a test agent.

The level of βTRP activity in a cell or other sample is determined and compared to a baseline value (e.g., a control value). Activity can be measured based on a crude extract or partially or essentially purified βTRP from a sample. Measurement of βTRP activity involves measuring cation (e.g., $Ca^{2+}$) channel activity, for example, as described in Lesage et al. *Am. J. Physiol. Renal. Physiol.* 279:F793–F801 (2000) and Girad et al., *Biochem. Biophys. Res. Commun.* 282: 249–256 (2001). For example, changes in ion flux may be assessed by determining changes in polarization (i.e., electrical potential) of the cell or membrane expressing a βTRP polypeptide. In some embodiments, changes in cellular polarization is monitored by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: $^{45}Ca^{2+}$ flux assays and fluorescence assays using voltage-sensitive dyes or ion sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing cation flux through the channel proteins comprising a βTRP polypeptide can be performed by application of the compounds to a bath solution in contact with and comprising cells having a channel of the present invention (see, e.g., Blatz et al., *Nature* 323:718–720 (1986); Park, *J. Physiol.* 481:555–570 (1994)).

The effects of the test compounds upon the function of the channels can be measured by changes in the electrical currents or ionic flux or by the consequences of changes in currents and flux. Changes in electrical current or ionic flux are measured by either increases or decreases in flux of ions such as calcium ions. The ions can be measured in a variety of standard ways. They can be measured directly by concentration changes of the ions, e.g., changes in intracellular concentrations, or indirectly by membrane potential or by radio-labeling of the ions or by using calcium-dependent fluorescent dyes.

Figure 3:
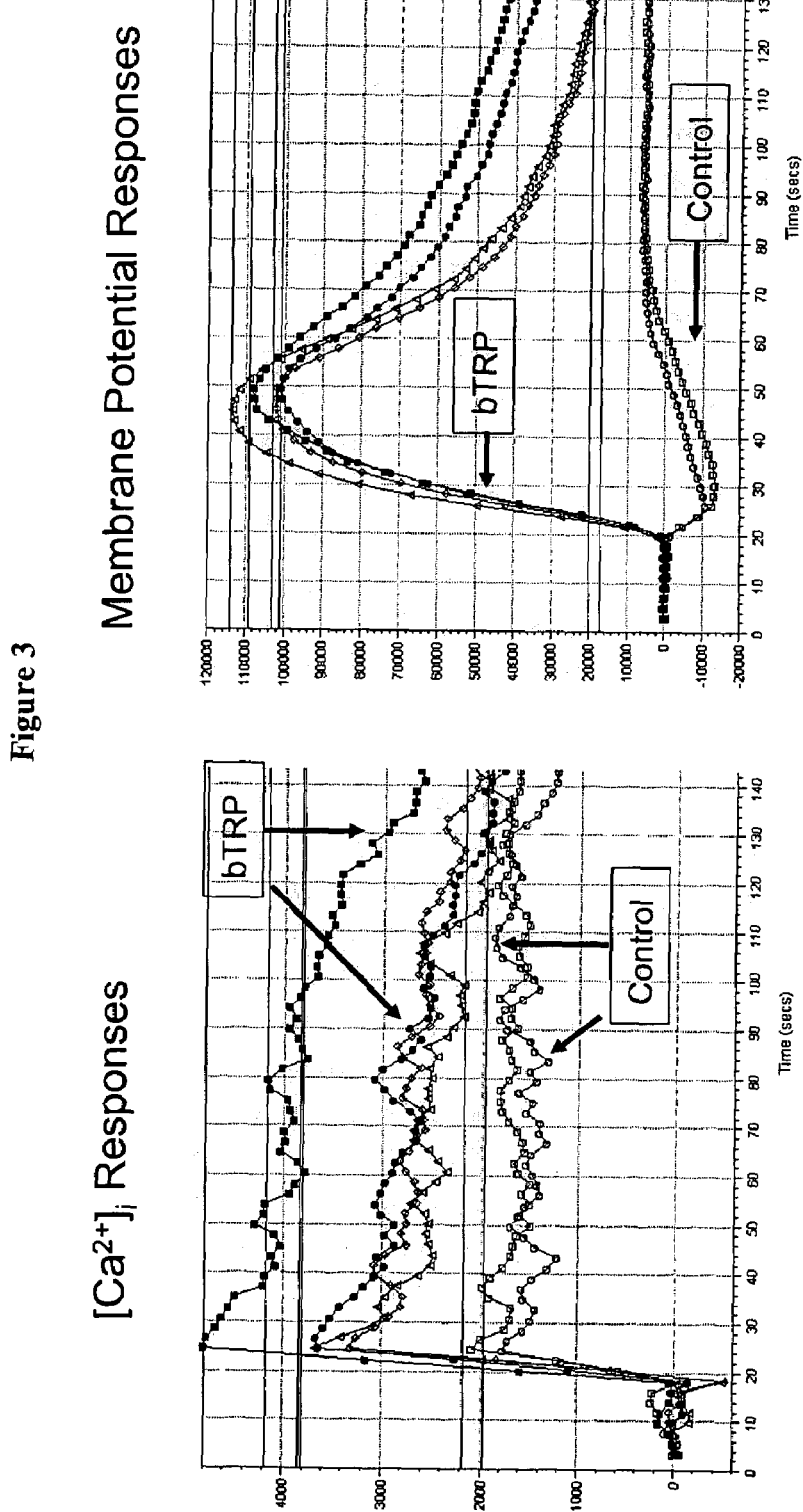
FIG. 3 displays intracellular free calcium $[Ca^{2+}]_i$ and membrane potential responses to ATP in CHO-K1 cells stably transfected with βTRP. Control and βTRP-CHO cells were plated in 96-well plates 2-d before the assay. $[Ca^{2+}]_i$ and membrane potential (MP) responses to ATP (30 μM added at 20 sec) were measured with FLEXStation® and correspondent dyes from Molecular Devices (Sunnyvale, Calif.).

As illustrated in FIG. 3, membrane potential provides a particularly clean signal:noise ratio compared to calcium flux measurements for measuring βTRP activity. Cell membrane depolarization upon activation of βTRP can be measured with membrane potential dependent fluorescent dyes such as cationic carbocyanines and rhodamines and anionic oxonols, as well as proprietary dyes available for the Molecular Devices (Sunnyvale, Calif.) FLEXstation® and FLIPR® systems. Fluorescence triggered by cell depolarization can be detected with devices known in the art, e.g., FLEXstation®.

Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release, intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, changes in intracellular second messengers such as cyclic nucleotides and modulation (e.g., decrease) of apoptosis.

4. Validation

Agents that are initially identified by any of the foregoing screening methods can be further tested to validate the apparent activity. In some embodiments, a βTRP activator is selected by any or all of the following criteria: (i) the activator induces a depolarization response specifically in a cell expressing a heterologous βTRP polypeptide (but not in cells not expressing βTRP); (ii) the activator is not suppressible by PLC inhibitors (i.e., is not activated by an upstream regulator of βTRP); and (iii) the activating effect of the activator is suppressible by TRP blockers such as 2-APB.

Validation assays can include, e.g., in vitro single cell imaging or patch clamping to confirm effects on ion flux. In vitro insulin secretion assays using isolated islet cells (normal or diabetic) can be performed in the presence or absence of the candidate activator.

In some embodiments, validation studies are conducted with suitable animal models. The basic format of such methods involves administering a lead compound identified during an initial screen to an animal that serves as a model for humans and then determining if βTRP is in fact modulated. The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty (ZDF) rats etc.) or polygenic models of diabetes (e.g., a high fat fed mouse model) can be useful for validating βTRP modulation and its effect in a diabetic animal.

Ideally, βTRP activation should enhance insulin secretion only in high glucose. Therefore, in some embodiments, a selected activator compound reduces hyperglycemia in ZDF rats and db/db mice and does not induce hypoglycemia in either diabetic or control animals.

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 or more different compounds are possible using the integrated systems of the invention. In addition, microfluidic approaches to reagent manipulation can be used.

The molecule of interest (e.g., βTRP or fragments thereof) can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest (e.g., βTRP or fragments thereof) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, poly-His, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:9). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of βTRP. Control reactions that measure βTRP activity of the cell in a reaction that does not include a potential modulator are optional, as the assays are highly uniform. Such optional control reactions are appropriate and increase the reliability of the assay. Accordingly, in one embodiment, the methods of the invention include such a control reaction. For each of the assay formats described, "no modulator" control reactions that do not include a modulator provide a background level of binding activity.

In some assays it will be desirable to have positive controls. At least two types of positive controls are appropriate. First, a known activator of βTRP of the invention can be incubated with one sample of the assay, and the resulting increase in signal resulting from an increased expression level or activity of βTRP are determined according to the methods herein. Exemplary activators include, e.g., calcimycin. Second, a known inhibitor of βTRP can be added, and the resulting decrease in signal for the expression or activity of βTRP can be similarly detected. Exemplary inhibitors include, e.g., 2-APB or U73122, a PLC inhibitor from Sigma Chemicals. It will be appreciated that modulators can also be combined with activators or inhibitors to find modulators that inhibit the increase or decrease that is otherwise caused by the presence of the known modulator of βTRP.

D. Computer-Based Assays

Yet another assay for compounds that modulate the activity of βTRP involves computer-assisted drug design, in which a computer system is used to generate a three-dimensional structure of βTRP based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions (e.g., the active site) of the structure that have the ability to bind ligands or otherwise be modulated. Similar analyses can be performed on potential receptors or binding partners of βTRP and can be used to identify regions of interaction with βTRP. These regions are then used to identify polypeptides that bind to βTRP.

Once the tertiary structure of a protein of interest has been generated, potential modulators can be identified by the computer system. Three-dimensional structures for potential modulators are generated by entering chemical formulas of compounds. The three-dimensional structure of the potential modulator is then compared to that of βTRP to identify binding sites of βTRP. Binding affinity between the protein and modulators is determined using energy terms to determine which ligands have an enhanced probability of binding to the protein.

V. Administration and Pharmaceutical Compositions

Modulators of βTRP (e.g., antagonists or agonists) can be administered directly to the mammalian subject for modulation of βTRP activity in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)).

The modulators (e.g., agonists or antagonists) of the expression or activity of βTRP, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

The modulators (e.g., agonists or antagonists) of the expression or activity of βTRP, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, βTRP modulators of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. *Prog. Drug Res.* (1998) 51: 33–94; Haffner, S. *Diabetes Care* (1998) 21: 160–178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165–71; United Kingdom Prospective Diabetes Study Group: UKPDS 28, *Diabetes Care* (1998) 21: 87–92; Bardin, C. W.,(ed.), *Current Therapy In Endocrinology And Metabolism*, 6th Edition (Mosby—Year Book, Inc., St. Louis, Mo. 1997); Chiasson, J. et al., *Ann. Intern. Med.* (1994) 121: 928–935; Coniff, R. et al., *Clin. Ther.* (1997) 19: 16–26; Coniff, R. et al., *Am. J. Med.* (1995) 98: 443–451; and Iwamoto, Y. et al., *Diabet. Med.* (1996) 13 365–370; Kwiterovich, P. *Am. J. Cardiol* (1998) 82(12A): 3U–17U). These studies indicate that modulation of diabetes, among other diseases, can be further improved by the addition of a second agent to the therapeutic regimen. Combination therapy includes administration of a single pharmaceutical dosage formulation that contains a βTRP modulator of the invention and one or more additional active agents, as well as administration of a βTRP modulator and each active agent in its own separate pharmaceutical dosage formulation. For example, a βTRP modulator and a thiazolidinedione can be administered to the human subject together in a single oral dosage composition, such as a tablet or capsule, or each agent can be administered in separate oral dosage formulations. Where separate dosage formulations are used, a βTRP modulator and one or more additional active agents can be administered at essentially the same time (i.e., concurrently), or at separately staggered times (i.e., sequentially). Combination therapy is understood to include all these regimens.

One example of combination therapy can be seen in modulating diabetes (or treating diabetes and its related symptoms, complications, and disorders), wherein the βTRP modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No. 5,859,037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose); amylin and amylin derivatives (such as pramlintide, (see, also, U.S. Pat. Nos. 5,902,726; 5,124,314; 5,175,145 and 6,143,718.)); insulin secretogogues (such as repaglinide, gliquidone, and nateglinide (see, also, U.S. Pat. Nos. 6,251,856; 6,251,865; 6,221,633; 6,174,856)), and insulin.

VI. Methods for Identifying Modulators of Polypeptides that Regulate βTRP

As illustrated in FIG. 3, activation of βTRP can be readily measured by detecting changes in membrane potential. Membrane potential-dependent fluorescent dyes provide significant signal that can be measured using devices useful in high throughput screening assays. To the inventors' knowledge, no channel in the TRP family has been described to provide such a clear, readily measurable membrane potential/cell depolarization signal upon activation. Moreover, it is not predictable that a calcium channel would mediate such a large change in membrane potential so as to be readily measured in assays other than patch clamping. Accordingly, the present invention provides methods of identifying modulators of polypeptides that regulate βTRP by identifying agents that induce a change in membrane potential in cells expressing βTRP.

In some embodiments, the methods comprise contacting an agent to a cell, wherein the cell expresses βTRP and an upstream regulator of βTRP; and detecting a change membrane potential of the cell, wherein a change in the membrane potential of the cell in the presence of the agent compared to the absence of the agent indicates that the agent modulates activity of the regulator. Exemplary regulators of βTRP include, e.g., G-protein coupled receptors (GPCRs) and G-proteins. For example, in some embodiments, the GPCR is selected from Gq, Gi and Gs receptors. Exemplary Gq receptors include, e.g., a muscarinic or PT2Y receptor. In embodiments involving the Gi receptors, a promiscuous G protein such as Gqi5, Galpha16, Gqs5, Gqo5, is also expressed in the cell to mediate signaling between the GPCR and βTRP.

The methods of the invention can comprise detecting changes in membrane potential using a device sufficient for high throughput screening. For instance, changes in membrane potential can be detected using cell-based assays in the presence of dyes that respond fluorescently to membrane potential changes. Because of the significant change in membrane potential induced by activation of βTRP, devices for measuring the fluorescence, such as the FLEXstation® and FLIPR® systems (Molecular Devices, Sunnyvale, Calif.) can be used to measure βTRP activation. These devices, in contrast to patch clamping techniques, are useful devices for high throughput screening. Thus, a significant number (e.g., at least 96, 384, 500, or 1000 or more) of potential modulators (e.g., in a combinatorial library) can be assayed for an effect on a regulator of βTRP in a single day by one person. Thus, large combinatorial libraries of compounds, as described herein can be screened to identify small molecules that modulate regulator activity.

In some embodiments, the regulator polypeptide and/or βTRP polypeptide are recombinantly expressed in a cell. Exemplary cells for recombinant expression include, e.g. mammalian cells (e.g., HEK293, CHO, Cos7), insect cells (e.g., sf21), bacterial cells (e.g., *E. coli*), or yeast (e.g., *Pichia* or *S. cervisiae*).

EXAMPLES

Example 1

This example demonstrates that βTRP is expressed in pancreatic islet cells and demonstrates that introduction of βTRP into islet cells of diabetic animals improves glucose stimulated insulin secretion.

Custom Affymetrix™ oligonucletide arrays were used to survey islet gene expression. Microarray probe set MBXRATISL12881 was called "Present" by the Affymetrix GeneChip™ analysis software in 5 independent rat islet mRNA samples and absent in 10 other tissues examined. The mouse probe set MBXMUSISL22609 also demonstrated a high degree of enrichment in islets and in the cultured beta cell line (betaHC9) mRNA samples relative to those of other tissues (FIG. 1B). Multiple clones for the corresponding cDNAs were found in human, rat and mouse islet libraries, and sequencing of these revealed that the encoded protein was a predicted TRP channel, which we named betaTRP. The human gene for betaTRP had been sequenced as part of an examination of the Beckwith- Wiedeman syndrome locus and had been named MTR1. See, PCT Application WO0132693. In contrast to the statements in PCT Application WO0132693, betaTRP ESTs are well represented in human, rat and mouse islet libraries. Oligonucleotide array data confirmed that pancreatic islets are highly enriched for betaTRP. In-situ hybridization was used to determine that betaTRP mRNA is abundant in the majority of the core cells of rat islets, which indicates that many if not most beta cells express betaTRP.

In an effort to identify genes that are functionally important for proper regulation of insulin secretion that are altered in the diabetic state we used a rat model of Type II diabetes. Custom rat islet array hybridization for the mRNA corresponding to betaTRP (probe set MBXRATISL12881) is reduced 2.4 fold in islets of diabetic (9 week old ZDF) rats relative to non-diabetic (9 week old ZLC) control animals (FIG. 1B). βTRP expression was substantially restored by concomitant treatment with troglitazone FIG. 1B). A similar result is observed in ZDF female rats fed a high fat diet. Beta TRP mRNA is also decreased greater than 2-fold in male ZDF rats at 9 weeks of age relative to lean control rats (data not shown)

Figure 2:
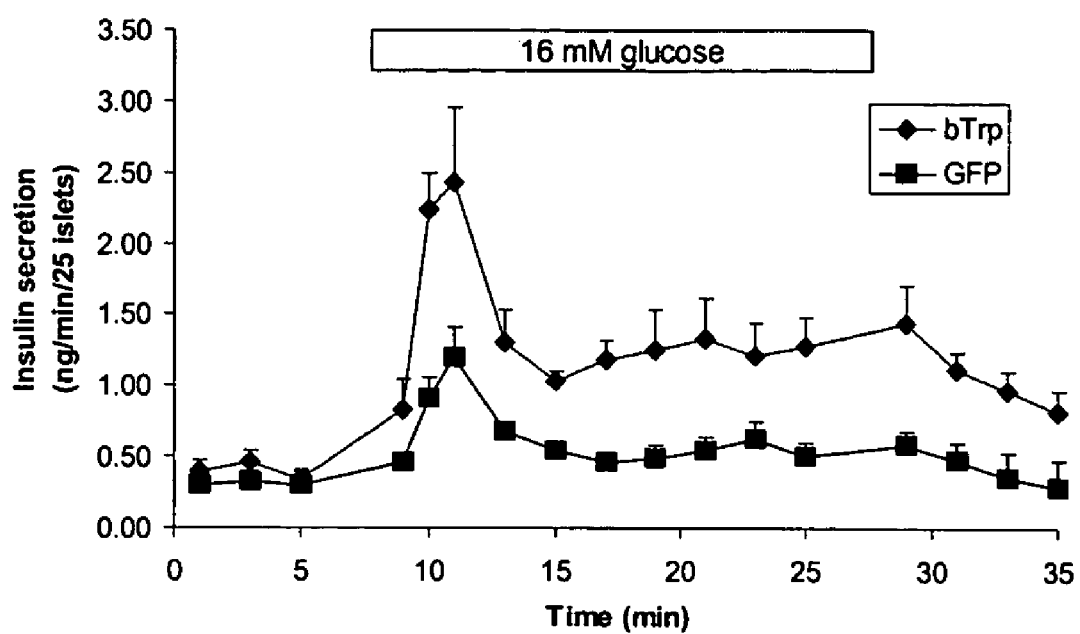
FIG. 2 illustrates insulin secretion in ZDF islets infected with Ad-βTRP virus. Islets from male ZDF rats were infected with an adenovirus expressing βTRP or eGFP and insulin responses to 16 mM glucose was determined by perifusion in Krebs-Ringers bicarbonate medium. Overexpression of βTRP in the ZDF islets enhanced both phases of the insulin secretion stimulated by glucose.

The islets from these diabetic animals are deficient in glucose stimulated insulin secretion (GSIS) relative to the islets of control animals. However, adenoviral expression of betaTRP in the ZDF islets restored their responsiveness to glucose in a static insulin secretion assay or in a islet perfusion experiment (FIG. 2). Expression of betaTRP did not increase basal insulin secretion and had little effect on islets from non-diabetic animals. These data indicate that the betaTRP deficiency found in ZDF islets is functionally linked to the decline in GSIS is these islets.

Example 2

This example demonstrates methods for high throughput screening of modulators of βTRP.

Activation (opening) of the pancreatic β cell cation channel βTRP represents a novel mechanism for enhancing glucose-stimulated insulin secretion in individuals with type II diabetes. Type II diabetes results when pancreatic beta cells are unable to compensate for the increased insulin demand caused by peripheral insulin resistance. Therapeutic agents such as sulphonylureas and meglitinides promote insulin secretion via the same molecular mechanism ($K_{ATP}$ channel closure) as the major pathway by which glucose regulates insulin secretion. Although these agents are widely used, they can be less than ideal in that they have intrinsic potential to cause hypoglycemia and also have significant rates of primary and secondary failure. Activation of mechanisms in the β cell that do not in themselves trigger insulin secretion but potentiate $Ca^{++}$ influx after glucose-dependent $K_{ATP}$ channel closure can enhance insulin secretion in a more physiologically appropriate manner. The βTRP cation channel represents a component of such a potentiator mechanism for enhancing $Ca^{++}$ influx and insulin secretion. This type of therapeutic approach also offers a novel therapy for diabetes patients for whom sulphonylureas/meglitinides fail.

The TRP family (of which βTRP is a member) includes a diverse group of proteins that share a common core domain that is similar to the channel-forming core of *Drosophila* TRP (Transient Receptor Potential), a light-activated $Ca^{2+}$-selective channel of the fly visual system. TRP channels mediate the influx of $Ca^{2+}$ and/or other cations when endoplasmic reticullum (ER) $Ca^{2+}$ stores are depleted or when receptors coupled to Gq and phospholipase-β (PLC) are activated. We have demonstrated that βTRP facilitates $Ca^{2+}$ influx in response to PLC activation and ER $Ca^{2+}$ store depletion when expressed in HEK293 and COS-1 cells.

The activation (opening) of βTRP (TRPM5) results a robust $Ca^{2+}$ influx and membrane depolarization which can be detected indirectly with specific fluorescent dyes for $Ca^{2+}$ and membrane potential (MP). FIG. 3 displays representative recordings of $[Ca^{2+}]_i$ and MP responses to ATP in control and βTRP-CHO cells. The MP response to ATP is present only in βTRP cells. As one option to execute high throughput screens for βTRP modulators, CHO-K1 based βTRP stable cell lines are used to screen for small molecule modulators using the Molecular Devices' FLIPR® (Molecular Devices, Sunnyvale, Calif.) membrane potential assay with minor modifications.

The goal of the screening is to find specific and director activators (openers) of βTRP channel. The activation of the channel is ideally complete and able to trigger a rise in $[Ca^{2+}]_i$ and plasma membrane depolarization of its host cells.

The following protocol is optimized for the measurement of membrane potential (MP) in 96-well format using Molecular Devices' Membrane Potential Dye (Cat #R-8034) on the FLEXStation (Molecular Devices). It is expected to be applicable or adaptable to the 384-well format assay with the FLIPR$^{384}$ system.

A CHO-K1 based stable cell line expressing βTRP (designated "Line A2-18" herein) is used for βTRP high throughput screening according to the follow protocol:
1. Seed A2–18 βTrp-CHO cell and the control line (A1-5) to 96-well plates.
2. Grow the cells for 24–48 h in DMEM medium to 85–95% confluency.
3. Prepare following reagents immediately before the assay:
   i. Assay buffer: dilute Component B of the FLIPR® assay kit and adjust pH to 7.4 with 1 N NaOH. No probenecid was needed.
   ii. MP dye: suspend a vial of Component A of the FLIPR® assay kit with 10 ml of the assay buffer.
   iii. Compound solutions: dilute DMSO stocks of the testing compounds to a 5× solution with the assay buffer. Raise $Ca^{2+}$ concentration in the compound solutions to 12.5 mM with 1 M $CaCl_2$.
4. Carefully remove the culture medium from all wells.
5. Add 50 μl assay buffer and 50 μl MP dye.
6. Incubate the plates at 37° C. for 30–60 minutes.
7. Set the FLEXStation to MP assay mode and to 37° C.
8. Transfer the cell plate and compound plate to FLEXStation.
9. Record baseline for 18 sec (Ex 530, Em560).
10. Add the 5× compound solutions to the cells and read another 100 sec.
11. Save and analyze data.

Reagent List
1. Assay buffer: Hank's Balanced Salt Solution (HBSS) with 20 mM Hepes, pH 7.4
2. MP dye: Molecular Devices Corporation, Cat#8034 (for FLIPR)
3. Positive control: ATP 10–100 μM (a purinergic receptor agonist) Calcimycin (A23187) 5–10 μM (a calcium ionophore)
4. Antagonist control:
   i. 2-APB 75 μM (from Tocris, TRP channel and IP3 receptor blocker);
   ii. U73122 10 μM (from Sigma Chemicals, PLC inhibitor).

Figure 4:
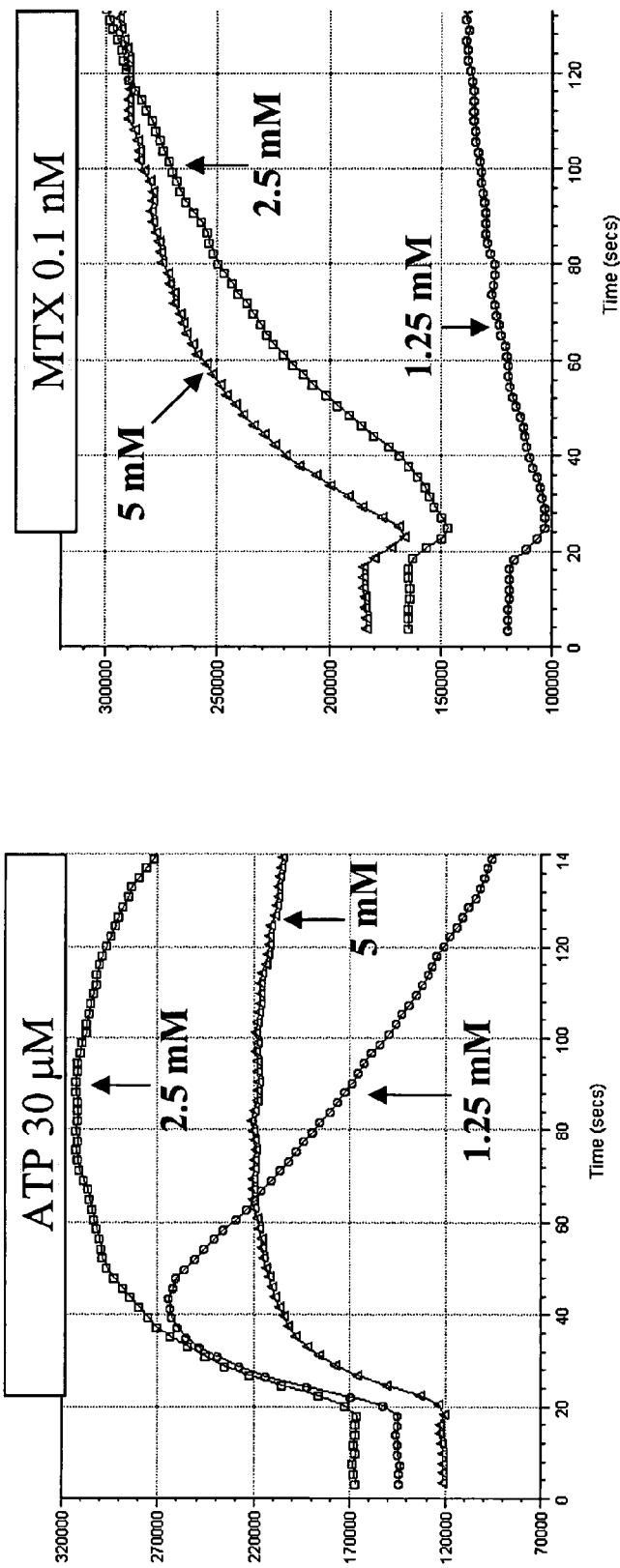
FIG. 4 illustrates MP responses to ATP and MTX at different $Ca^{2+}$ levels in βTRP-CHO cells. MP responses to Maitotoxin (MTX) were monitored with the Flexstation® as described in FIG. 3. The regular assay buffer contains 1.26 mM $Ca^{2+}$. To raise the calcium concentration to 2.5 or 5 mM, extra amount of $CaCl_2$ was added at same time as other testing reagents.

Other Experimental Conditions
1. The Cells:
   iii. Maintenance: DMEM with 10% FCS and 200 µg/ml G418; Passaged 1–2 time/week with trypsin-EDTA.
   iv. Confluency: 85–95% by the time of assay.
   v. Plating: Regular or pre-coated plates; 24–48 h before assay.
   vi. Passage: up to the $10^{th}$ passage.
2. $Ca^{2+}$ concentration in the assay system:
   The relative low $Ca^{2+}$ (1.26 mM) in Molecular Device's original assay systems may limit the influx of extracellular $Ca^{2+}$ through TRP channel and the accompanied depolarization as suggested by the lack of action of maitotoxin (MTX) in βTRP-CHO cells. MTX is a marine polyether toxin known to be a direct activation of non-selective cation channels (including βTRP). Raising $Ca^{2+}$ concentration to 2.5–5 mM in the assay system significantly enhanced the ability for the MP and the Calcium Assay Kits to detect the increase in $[Ca^{2+}]_i$ or MP induced by MTX (FIG. 4).

Example 3

Figure 5:
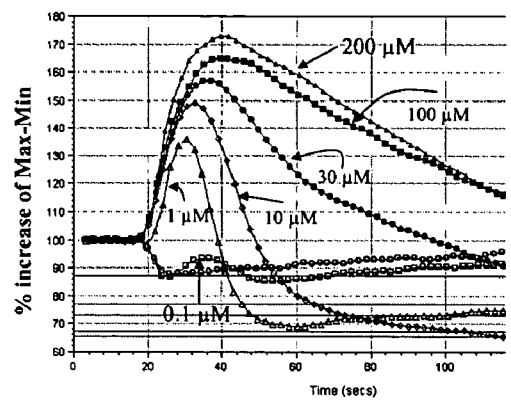
FIG. 5 illustrates dose dependent effects of ATP and calcimycin on membrane potential in βTRP-CHO cells. MP was measured with Flexstation® as in FIG. 3. No effect was observed in control cells for either compound.
Figure 5:
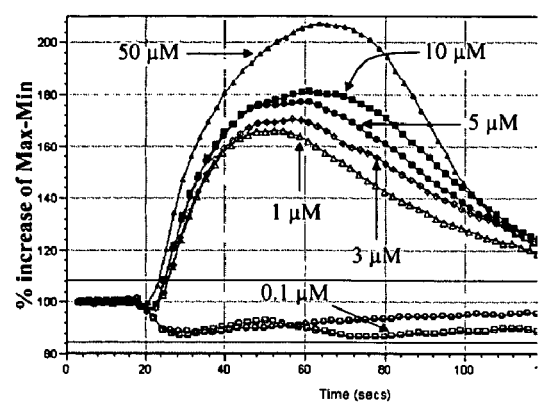

This Example demonstrates solvent dose responses and responses to other channel modulators.
   Effect of DMSO
   In the FLEXStation assay, upon the addition of the testing compound (a 25 µl of compound solution was added to each well which contains 100 vl of diluted dye) the CHO-βTRP cells tend to lose some intensity of fluorescent signal. The drop in RFU signal was indistinguishable between the assay buffer and low concentration of DMSO (<0.5%), but was significantly exaggerated by 2.5% DMSO (FIG. 5). On the other hand, we did not observe any non-specific depolarization responses to DMSO.

Example 4

Figure 6:
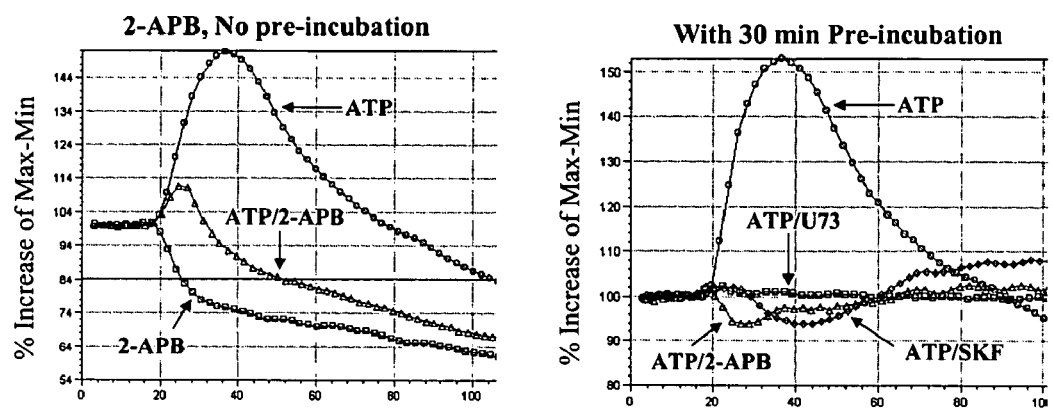
FIG. 6 illustrated the effects of known TRP blockers on ATP-induced depolarization in βTRP-CHO cells. MP was measured with Flexstation® as in FIG. 3. The inhibitors were added either simultaneously (right panel) or prior to ATP stimulation (left panel).

This Example provides positive controls useful in the assays of the invention.
   Effects of Other Channel Modulators on MP of the bTRP-CHO Cells
   To test the specificity of the depolarization responses to ATP in the bTRP-CHO cells, we tested the effects of 80 compounds from the Sigma-RBI Ion Channel Modulators Ligand-Set (Sigma #L6912) in both control (A1-5) and a βTRP-CHO cell line (A2-18). The Sigma ligand-set consists of modulators of multiple members of the $K^+$, $Na^+$, $Ca^{2+}$ and $Cl^-$ channels, as well as several channel forming amino acid transpoters. Among the 80 compounds, only A23187 (Calcimycin) induced a βTRP cell specific depolarization similar to ATP. Calcimycin is a $Ca^{2+}$ ionophore known to be able to deplete intracellular $Ca^{2+}$ stores. In addition, the class-III antiarrythmic compound Clofilium also triggered depolarization in both control and bTRP cells. The mechanism of clofilium is not known.
   Activator Control for TRP Channel
   ATP and calcimycin dose-dependently induced depolarization in βTRP-CHO cells, but not in control cells, as expected (FIG. 6). The estimated $EC_{50}$ of ATP and calcimycin is 11 and 0.8 µM respectively. ATP activates TRP channels by generating IP3 through the Gq-coupled P2Y receptor, whereas calcimycin acts by a direct depletion of intracellular $Ca^{2+}$ stores.

Example 5

This Example provides negative (antagonist) controls useful in the assays of the invention.
   The MP responses to ATP and calcimycin were suppressed over 50% by 2-APB when it was added to the cells at the same time as the two stimuli. 2-APB is known to blocker the IP3 receptor on the ER (ligand-gated $Ca^{2+}$ channel) and TRP channels in the plasma membrane. The effect of ATP on MP in βTRP-CHO cells was also inhibited by a 30 minute pre-incubation of the cells with the PLC inhibitor U73122 (FIG. 6).
   It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying an agent that induces glucose-stimulated insulin production in an animal, the method comprising the steps of:
   (i) contacting an agent to a functional cation channel polypeptide comprising an amino acid sequence at least 80% identical to SEQ ID NO:2, and wherein the polypeptide is expressed in a cell and the contacting step comprises contacting the agent to the cell;
   (ii) selecting an agent that induces a differential change in electrical potential of the plasma membrane of the cell compared to the change in electrical potential of the plasma membrane of a cell contacted to the agent when:
   the activity of the functional cation channel polypeptide is inhibited; or
   the functional cation channel polypeptide is not expressed,
   thereby indicating that the differential change is a result of contacting the agent to the polypeptide, and
   (iii) determining if the agent selected in step (ii) enhances glucose-stimulated insulin secretion, thereby identifying an agent that induces glucose-stimulated insulin production in an animal.

2. The method of claim 1, wherein the polypeptide comprises SEQ ID NO:2.

3. The method of claim 1, wherein an agent is selected that enhances polypeptide activity and the activity of the polypeptide is determined by a step comprising measuring a change in calcium flux in the cell.

4. The method of claim 1, wherein the membrane potential of the cell is measured be detecting a change in fluorescence of a dye whose fluorescence is dependent on cell depolarization and wherein the change in fluorescence is detected with a device sufficient for high throughput screening.

5. The method of claim 1, wherein the cell is a pancreatic β cell.

6. The method of claim 1, wherein the polypeptide is recombinantly expressed in the cell.

7. The method of claim 1, wherein the polypeptide comprises an amino acid sequence at least 90% identical to SEQ ID NO:2.

8. The method of claim 1, wherein the determining step is carried out in vitro.

9. The method of claim 1, wherein the determining step is carried out in vivo.

* * * * *